(12) United States Patent
Gysling et al.

(10) Patent No.: US 7,367,240 B2
(45) Date of Patent: *May 6, 2008

(54) APPARATUS AND METHOD FOR PROVIDING A FLOW MEASUREMENT COMPENSATED FOR ENTRAINED GAS

(75) Inventors: Daniel L. Gysling, Glastonbury, CT (US); Douglas H. Loose, Southington, CT (US)

(73) Assignee: CiDRA Corporation, Wallingford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/656,848

(22) Filed: Jan. 22, 2007

(65) Prior Publication Data

US 2007/0151365 A1 Jul. 5, 2007

Related U.S. Application Data

(63) Continuation of application No. 10/766,440, filed on Jan. 27, 2004, now Pat. No. 7,165,464, which is a continuation-in-part of application No. 10/715,197, filed on Nov. 17, 2003, now abandoned.

(60) Provisional application No. 60/426,723, filed on Nov. 15, 2002, provisional application No. 60/441,395, filed on Jan. 21, 2003, provisional application No. 60/441,652, filed on Jan. 22, 2003, provisional application No. 60/442,968, filed on Jan. 27, 2003, provisional application No. 60/503,349, filed on Sep. 16, 2003, provisional application No. 60/518,171, filed on Nov. 7, 2003.

(51) Int. Cl.
*G01F 1/34* (2006.01)
*G01N 29/00* (2006.01)

(52) U.S. Cl. .................. 73/861.42; 73/61.49

(58) Field of Classification Search ............. 73/861.42, 73/61.49
See application file for complete search history.

(56) References Cited

U.S. PATENT DOCUMENTS 2,874,568 A 2/1959 Peterman (Continued)

FOREIGN PATENT DOCUMENTS

WO WO 93/14382 7/1993

(Continued)

OTHER PUBLICATIONS

Sonar-Based Volumetric Flow Meter for Pulp and Paper Applications—By: Daiel L. Gysling & Douglas H. Loose—Dec. 3, 2002.

(Continued)

*Primary Examiner*—Harshad Patel

(57) ABSTRACT

A apparatus 10, 110 is provided that measures the speed of sound and/or vortical disturbances propagating in a fluid or mixture having entrained gas/air to determine the gas volume fraction of the flow 12 propagating through a pipes and compensating or correcting the volumetric flow measurement for entrained air. The GVF meter includes and array of sensor disposed axially along the length of the pipe. The GVF measures the speed of sound propagating through the pipe and fluid to determine the gas volume fraction of the mixture using array processing. The GVF meter can be used with an electromagnetic meter and a consistency meter to compensate for volumetric flow rate and consistency measurement respective, to correct for errors due to entrained gas/air.

23 Claims, 21 Drawing Sheets

U.S. PATENT DOCUMENTS

| | | | |
|---|---|---|---|
| 4,004,461 A | 1/1977 | Lynworth | |
| 4,048,853 A | 9/1977 | Smith et al. | |
| 4,080,837 A | 3/1978 | Alexander et al. | |
| 4,195,517 A | 4/1980 | Kalinoski et al. | |
| 4,248,085 A | 2/1981 | Coulthard | |
| 4,445,389 A | 5/1984 | Potzick et al. | |
| 4,896,540 A | 1/1990 | Shakkottai et al. | |
| 5,040,415 A | 8/1991 | Barkhoudarian | |
| 5,083,452 A | 1/1992 | Hope | |
| 5,218,197 A | 6/1993 | Carroll | |
| 5,285,675 A | 2/1994 | Colgate et al. | |
| 5,367,911 A | 11/1994 | Jewell et al. | |
| 5,398,542 A | 3/1995 | Vasbinder | |
| 5,524,475 A | 6/1996 | Kolpak et al. | |
| 5,526,844 A | 6/1996 | Kamen et al. | |
| 5,591,922 A | 1/1997 | Segeral et al. | |
| 5,741,980 A | 4/1998 | Hill et al. | |
| 5,770,805 A | 6/1998 | Castel | |
| 5,770,806 A | 6/1998 | Hiismaki | |
| 5,835,884 A | 11/1998 | Brown | |
| 5,845,033 A | 12/1998 | Berthold et al. | |
| 5,856,622 A | 1/1999 | Yamamoto et al. | |
| 5,948,959 A | 9/1999 | Peloquin | |
| 6,016,702 A | 1/2000 | Maron | |
| 6,151,958 A | 11/2000 | Letton et al. | |
| 6,202,494 B1 | 3/2001 | Riebel et al. | |
| 6,354,147 B1 | 3/2002 | Gysling et al. | |
| 6,378,357 B1 | 4/2002 | Han et al. | |
| 6,397,683 B1 | 6/2002 | Hagenmeyer et al. | |
| 6,435,030 B1 | 8/2002 | Gysling et al. | |
| 6,443,226 B1 | 9/2002 | Diener et al. | |
| 6,450,037 B1 | 9/2002 | McGuinn et al. | |
| 6,463,813 B1 | 10/2002 | Gysling | |
| 6,532,827 B1 | 3/2003 | Ohnishi | |
| 6,536,291 B1 | 3/2003 | Gysling et al. | |
| 6,550,342 B2 | 4/2003 | Croteau et al. | |
| 6,558,036 B2 | 5/2003 | Gysling et al. | |
| 6,587,798 B2 | 7/2003 | Kersey et al. | |
| 6,601,458 B1 | 8/2003 | Gysling et al. | |
| 6,609,069 B2 | 8/2003 | Gysling | |
| 6,691,584 B2 | 2/2004 | Gysling et al. | |
| 6,698,297 B2 | 3/2004 | Gysling | |
| 6,732,575 B2 | 5/2004 | Gysling et al. | |
| 6,782,150 B2 | 8/2004 | Davis et al. | |
| 6,813,962 B2 | 11/2004 | Gysling et al. | |
| 6,837,098 B2 | 1/2005 | Gysling et al. | |
| 6,862,920 B2 | 3/2005 | Gysling et al. | |
| 6,868,737 B2 | 3/2005 | Croteau et al. | |
| 6,889,562 B2 | 5/2005 | Gysling et al. | |
| 6,898,541 B2 | 5/2005 | Gysling et al. | |
| 7,058,549 B2* | 6/2006 | Gysling et al. | 73/861.18 |
| 7,062,976 B2* | 6/2006 | Gysling et al. | 73/861.18 |
| 7,134,320 B2* | 11/2006 | Gysling et al. | 73/861.18 |
| 7,165,464 B2* | 1/2007 | Gysling et al. | 73/861.42 |
| 2002/0095263 A1 | 7/2002 | Gysling et al. | |
| 2002/0123852 A1 | 9/2002 | Gysling et al. | |
| 2002/0129662 A1 | 9/2002 | Gysling et al. | |
| 2003/0038231 A1 | 2/2003 | Bryant et al. | |
| 2003/0136186 A1 | 7/2003 | Gysling et al. | |
| 2003/0154036 A1 | 8/2003 | Gysling et al. | |
| 2004/0016284 A1 | 1/2004 | Gysling et al. | |
| 2004/0069069 A1 | 4/2004 | Gysling et al. | |
| 2004/0074312 A1 | 4/2004 | Gysling | |
| 2004/0144182 A1* | 7/2004 | Gysling et al. | 73/861.42 |
| 2004/0167735 A1 | 8/2004 | Rothman et al. | |
| 2004/0194539 A1 | 10/2004 | Gysling | |
| 2004/0199340 A1 | 10/2004 | Kersey et al. | |
| 2004/0210404 A1 | 10/2004 | Gysling et al. | |
| 2004/0231431 A1 | 11/2004 | Bailey et al. | |
| 2004/0255695 A1 | 12/2004 | Gysling et al. | |
| 2005/0000289 A1 | 1/2005 | Gysling et al. | |
| 2005/0005711 A1 | 1/2005 | Gysling et al. | |
| 2005/0005712 A1 | 1/2005 | Gysling et al. | |
| 2005/0005713 A1 | 1/2005 | Winston et al. | |
| 2005/0011258 A1 | 1/2005 | Gysling et al. | |
| 2005/0011283 A1 | 1/2005 | Gysling et al. | |
| 2005/0011284 A1 | 1/2005 | Gysling et al. | |
| 2005/0012935 A1 | 1/2005 | Kersey | |
| 2005/0033545 A1 | 2/2005 | Gysling | |
| 2005/0039520 A1 | 2/2005 | Davis et al. | |
| 2005/0044929 A1 | 3/2005 | Gysling et al. | |
| 2005/0044966 A1 | 3/2005 | Gysling et al. | |
| 2005/0050956 A1 | 3/2005 | Gysling et al. | |
| 2005/0072216 A1 | 4/2005 | Engel | |
| 2005/0125166 A1 | 6/2005 | Loose et al. | |
| 2007/0044571 A1* | 3/2007 | Gysling et al. | 73/861.18 |
| 2007/0125154 A1* | 6/2007 | Gysling et al. | 73/861.356 |

FOREIGN PATENT DOCUMENTS

| | | |
|---|---|---|
| WO | WO 99/67629 | 12/1999 |
| WO | WO 02/46705 | 6/2002 |

OTHER PUBLICATIONS

Sonar-Based Volumetric Flow Meter for Chemical and Petrochemical Applications—By: Daniel L. Gysling & Douglas H. Loose—Feb. 14, 2003.

Piezo Film Sensors Technical Manual—Measurement Specialties, Inc. Apr. 2, 1999.

2004, U.S. Appl. No. 10/512,401, filed Oct. 22, 2004, pending.
2003, U.S. Appl. No. 10/712,818, filed Nov. 12, 2003, pending.
2003, U.S. Appl. No. 10/712,833, filed Nov. 12, 2003, pending.
2004, U.S. Appl. No. 10/762,409, filed Jan. 21, 2004, pending.
2004, U.S. Appl. No. 10/909,593, filed Aug. 2, 2004, pending.

"Noise and Vibration Control Engineering Principles and Applications", Leo L. Beranek and Istvan L. Ver, A. Wiley Interscience Publication, pp. 557-541, Aug. 1992.

"Two Decades of Array Signal Processing Research, The Parametric Approach", H. Krim and M. Viberg, IEEE Signal Processing Magazine, Jul. 1996, pp. 67-94.

"Development of an array of pressure sensors with PVDF film, Experiments in Fluids 26", Jan. 8, 1999, Springer-Verlag.

"Viscous Attenuation of Acoustic Waves in Suspensions" by R.L. Gibson, Jr. and M.N. Toksoz.

* cited by examiner

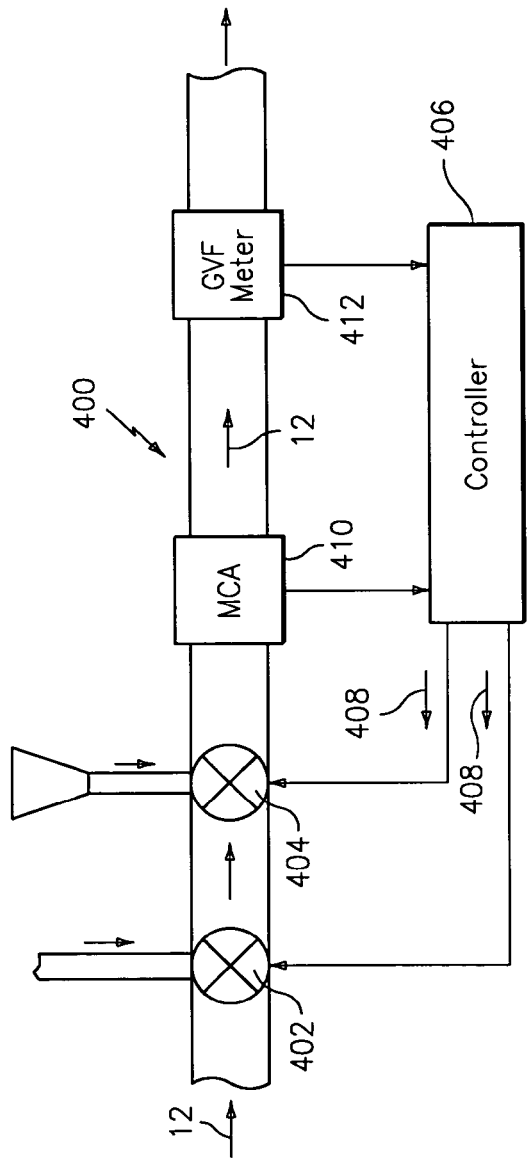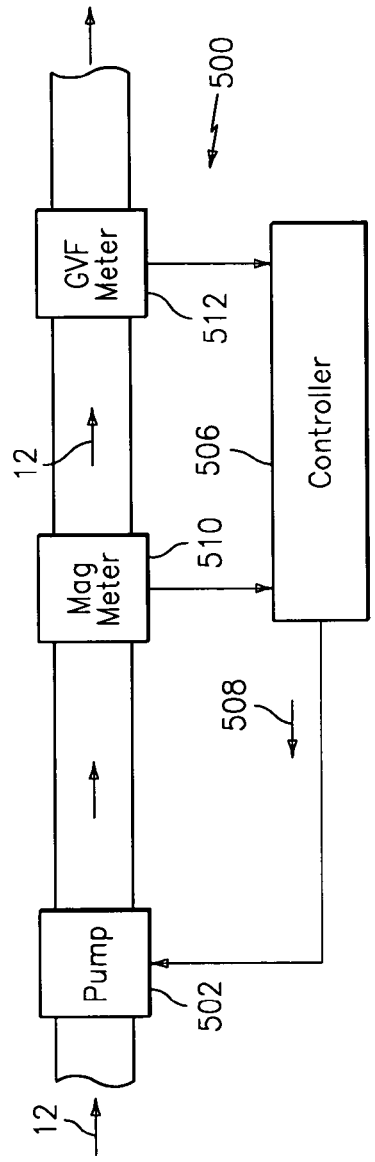
FIG. 23
FIG. 24

APPARATUS AND METHOD FOR PROVIDING A FLOW MEASUREMENT COMPENSATED FOR ENTRAINED GAS

CROSS-REFERENCE TO RELATED PATENT APPLICATIONS

This application is a continuation of U.S. patent application Ser. No. 10/766,440, filed on Jan. 27, 2004, now U.S. Pat. No. 7,165,464 which is a continuation in part of U.S. patent application Ser. No. 10/715,197, filed on Nov. 17, 2003, now abandoned which claimed the benefit of U.S. Provisional Application No. 60/426,723, filed Nov. 15, 2002; U.S. Provisional Application No. 60/441,395, filed Jan. 21, 2003, U.S. Provisional Application No. 60/441,652, filed Jan. 22, 2003; U.S. Provisional Application No. 60/442,968, filed Jan. 27, 2003, U.S. Provisional Application No. 60/503,349, filed Sep. 16, 2003; and U.S. Provisional Application No. 60/518,171, filed Nov. 7, 2003, all of which are incorporated herein by reference in their entirety.

TECHNICAL FIELD

This invention relates to an apparatus for measuring a flow having entrained gas therein, and more particularly to an apparatus that measures the speed of sound propagating through the flow to determine the gas volume fraction of the gas in the process flow and compensating the output measurement of a flow meter (e.g., a volumetric flow meter and a consistency meter) for entrained gas.

BACKGROUND ART

The present invention provides an apparatus and method of measuring volumetric flow rate and gas volume fraction in slurries used in the paper and pulp industries and in other industries. Slurries commonly used in the paper and pulp industry are mostly water and typically contain between 1% and 10% pulp content by mass. Monitoring the flow rate and consistency of the slurry can lead to improved quality and efficiency of the paper production process.

Processes run in the paper and pulp industry can often, either intentionally or unintentionally, entrain gas/air. Typically, this entrained air results in measurement errors in process monitoring equipment such as volumetric flow measurements and consistency meters.

Industry estimates indicate that entrained air levels of 2-4% are common. Since most process flow monitors are unable to distinguish between air and liquid, interpreting their output as liquid flow rates would result in a overestimate of the liquid by the volumetric flow rate of the air present at the measurement location. Similarly, for the void fraction of the air within the pipe can cause errors in consistency measurements.

Thus, providing a method and apparatus for measuring entrained air in paper and pulp slurries would provide several benefits. Firstly, it would provide a means to screen the output of process instrumentation. Secondly, in addition to screening the measurements, an accurate measurement of the entrained air would provide a means to correct the output of volumetric flow meters and consistency meters. Thirdly, monitoring variations in the amount of entrained air in a given process could be indicative of process anomalies, such a worn bushing or cavitating pumps and/or valves.

Multiphase process flow rate is a critical process control parameter for the paper and pulp industry. Knowing the amounts of liquid, solids and entrained gases flowing in process lines is key to optimizing the overall the papermaking process (Matula, 2000). Unfortunately, significant challenges remain in the achieving accurate, reliable, and economical monitoring of multiphase flow rates of paper and pulp slurries. Reliability challenges arise due the corrosive and erosive properties of the slurry. Accuracy challenges stem from the multiphase nature of the slurries. Economical challenges arise from the need to reduce total life time cost of flow measurement, considering installation and maintenance costs in addition to the initial cost of the equipment.

Currently, there is an unmet need for multiphase flow measurement in the paper and pulp industry. Real time flow measurement is typical restricted to monitoring the total volumetric flow rate in a process line without providing information on the composition of the process mixture. For example, electromagnetic flow meters are the most widely used flow meters in the paper and pulp industry, however they provide no indication of presence of entrained air, with its presence resulting in an over prediction of the volumetric flow of process fluid by the amount of air entrained. Consistency meter provide a measurement of the percentage of solids within the process, however this technology remains more of an art than a science. Furthermore, although entrained air is known to have a large, often deleterious, impact on the paper making process, instrumentation is currently not available to provide this measurement on a real time basis.

The present invention an accurate, reliable multiphase flow measurement in the paper and pulp industry.

In one embodiment of the present invention, the apparatus and method improves the determination of consistency of paper and pulp slurries. Consistency refers to the mass fraction of pulp contained in water and pulp slurries used in the paper making process. Consistency measurements are critical in the optimization of the paper making process. Currently, many companies produce consistency meters employing various technology to serve the paper and pulp industry. Unfortunately, accurate and reliable measurement of consistency remains an elusive objective. Typically, interpreting the output of a consistency meter in terms of actual consistency is more of an art than a science.

Of the various types of consistency meters on the market, microwave based meters may represent the best the solution for many applications. One such microwave-based consistency meter is manufactured by Toshiba. Microwave consistency meters essentially measure speed or velocity the microwave signal propagates through the medium being measured. For example, the speed of the microwave signal through water is approximately 0.1 time the speed of light in a vacuum (c), through air is approximately 1.0 times the speed of light in a vacuum, and through fiber (or pulp) is approximately 0.6 times the speed of light in a vacuum.

The velocity of the microwave signal propagating through the paper pulp slurry is measure by the conductive effects of the slurry, in accordance with the following equation:

$$V = c * \mathrm{sqrt}(E)$$

Where V is the velocity of the microwave signal propagating through the slurry, c is the speed of light in a vacuum, and E is the relative conductivity of the material. Typical values of relative conductivity for material comprising a paper/pulp slurry, for example, are:

Water relative conductivity=80;

Air relative conductivity=1; and

Fiber relative conductivity=3.

These meters typically work well in the absence of entrained air. With entrained air present, the air displaces water and looks like additional pulp fiber to the microwave meter. Thus, uncertainty in the amount of entrained air translates directly into uncertainty in consistency.

SUMMARY OF THE INVENTION

Objects of the present invention include an apparatus having sensor for determining the speed of sound propagating within a pipe for determining the gas volume fraction of a process flow to correct the output of a meter for entrained gas, such as a volumetric flow meter and a consistency meter.

According to the present invention, an apparatus for measuring a parameter of a process flow flowing within a pipe includes a first meter portion and a second meter portion. The first meter portion provides a meter measurement signal indicative of a parameter of the flow propagating through the pipe. The second meter portion includes a sensor for providing sound measurement signal indicative of the speed of sound propagating within the pipe. A processor provides a compensated meter measurement signal indicative of a measurement parameter corrected for entrained gas in the flow propagating through the pipe, in response to meter measurement signal and the sound measurement signal.

The foregoing and other objects, features and advantages of the present invention will become more apparent in light of the following detailed description of exemplary embodiments thereof.

BRIEF DESCRIPTION OF THE DRAWINGS

FIG. 23 is a block diagram of a closed loop system having a microwave consistency meter compensated for entrained gas, in accordance with the present invention.

FIG. 24 is a block diagram of a closed loop system having an electromagnetic flow meter compensated for entrained gas, in accordance with the present invention.

BEST MODE FOR CARRYING OUT THE INVENTION

Figure 1:
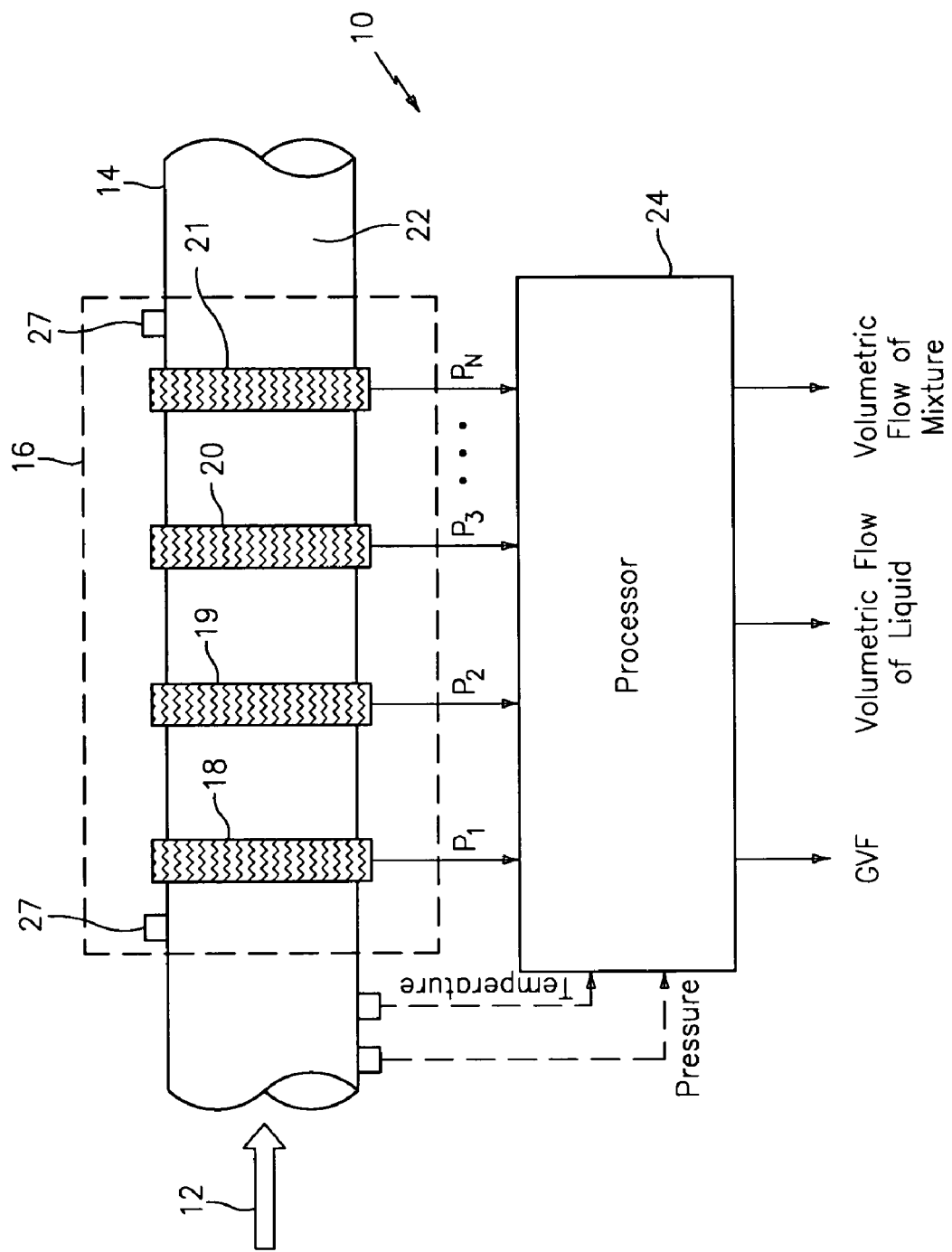
FIG. 1 is a schematic illustration of an apparatus having an array of sensors onto a pipe for measuring the volumetric flow and gas volume fraction of the mixture flowing in the pipe having entrained gas/air therein, in accordance with the present invention.

Referring to FIG. 1, an apparatus, generally shown as 10, is provided to measure volumetric flow rate and gas volume fraction in liquids and mixtures (e.g. paper and pulp slurries or other solid liquid mixtures) having entrained gas therein (including air). The apparatus 10 in accordance with the present invention determines the speed at which sound propagates within a pipe 14 to measure entrained gas in liquids and/or mixtures 12. To simplify the explanation of the present invention the flow propagating through the pipe will be referred to as a mixture or slurry with the understanding that the flow may be a liquid or any other mixture having entrained gas therein.

The following approach may be used with any technique that measures the sound speed of a fluid. However, it is particularly synergistic with sonar based volumetric flow meters such as described in U.S. Pat. No. 6,889,562 and U.S. Pat. No. 6,609,069, which are incorporated herein by reference, in that the sound speed measurement, and thus gas volume fraction measurement, can be accomplished using the same hardware as that required for the volumetric flow measurement. It should be noted, however, that the gas volume fraction measurement could be performed independently of a volumetric flow measurement, and would have utility as an important process measurement in isolation or in conjunction with other process measurements, which will be described in greater detail hereinafter.

Figure 2:
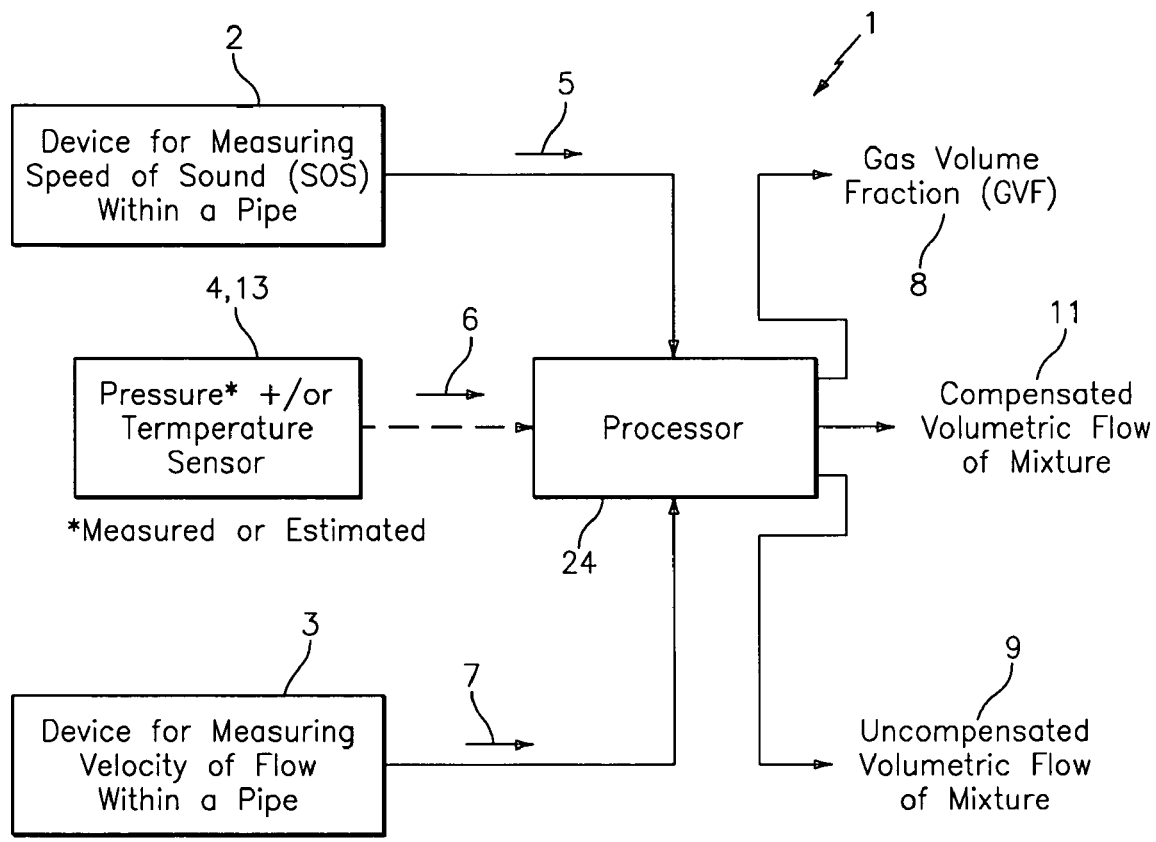
FIG. 2 is a block diagram of an embodiment of the apparatus of FIG. 1, in accordance with the present invention.

FIG. 2 is a block diagram 1 of the apparatus 10 of FIG. 1 that includes a device 2 for measuring the speed of sound (SOS) propagating within a pipe 14 and a device 3 for measuring the velocity of the mixture 12 within the pipe 14. A pressure sensor 4 and/or temperature sensor 13 measures the pressure and/or temperature of the mixture flowing through the pipe. Alternatively, the pressure and/or temperature may be estimated rather than actually measured. In response to the speed of sound signal 5, the velocity 7 of the flow 12 and characteristics 6 of the flow (e.g., pressure and temperature), a processor 24 determines the gas volume fraction (GVF) of the flow 12, the uncompensated volumetric flow 9 of the mixture, and the volumetric flow 11 of the flow compensated for the entrained air therein.

Figure 3:
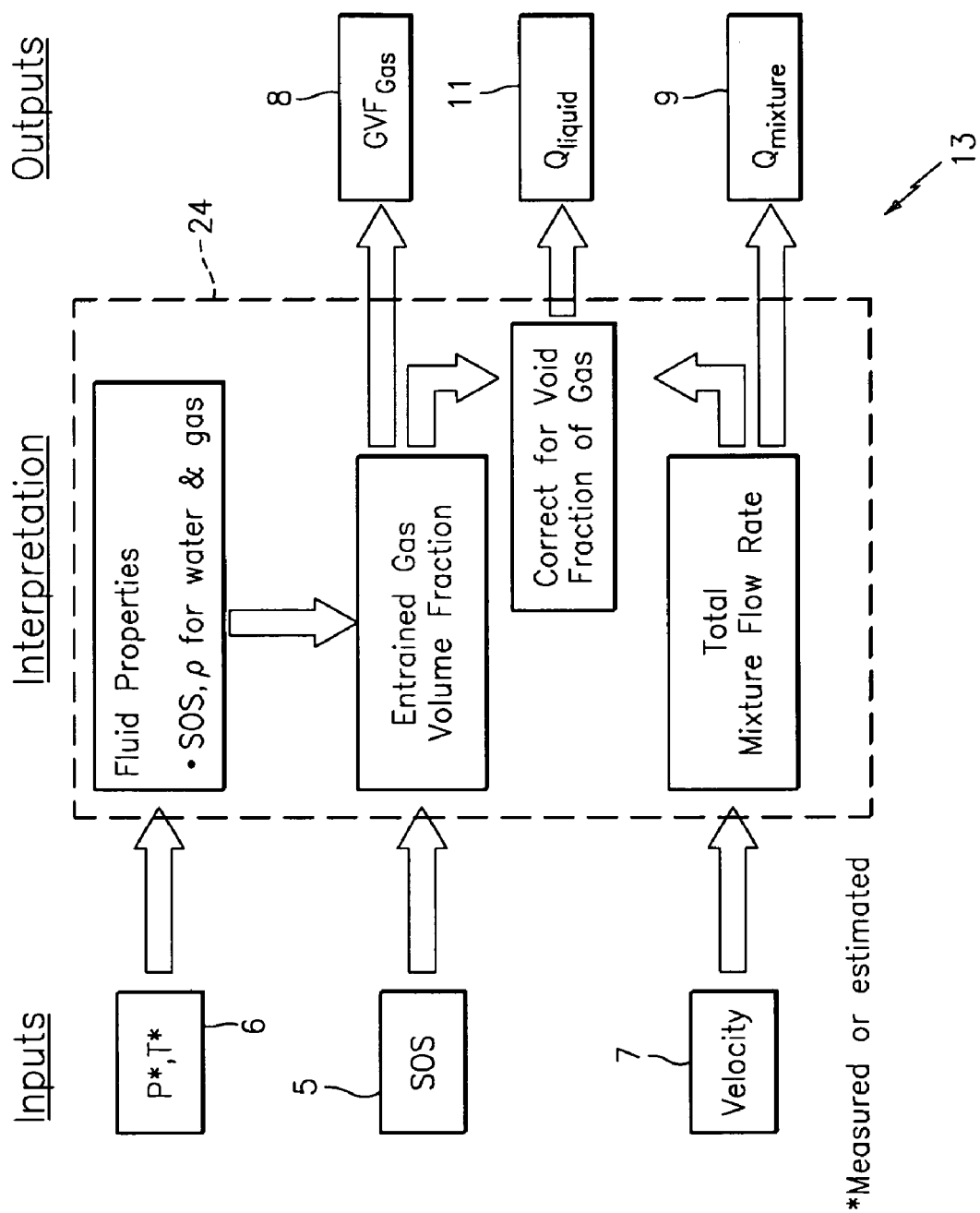
FIG. 3 is a functional flow diagram of an apparatus embodying the present invention that compensates the volumetric flow measurement of a volumetric flow meter, in accordance with the present invention.

A flow chart 13 shown in FIG. 3 illustrates the function of the processor 24. As shown in FIG. 2, the inputs to the processor includes the speed of sound (SOS) within the pipe 14, the velocity 7 of the mixture 12, and the pressure and temperature 6 of the mixture. The fluid properties of the mixture (e.g., SOS and density) are determined knowing the pressure and temperature of the mixture. The gas volume fraction of the mixture (GVF) is determined using the SOS measurement and fluid properties, which will be described in greater detail hereinafter. The volumetric flow rate of the mixture (including the entrained gas) is determined using the velocity and knowing the cross-sectional area of the inner diameter of the pipe. The processor 24 provides a compensated volumetric flow measurement of the mixture by correcting the uncompensated volumetric flow rate using the void fraction of the air. For example, correction for void fraction of gas may be as follows, for a no slip, homogeneous flow model:

$$Q\text{air} + Q\text{liquid} = Q\text{mix}$$

$$Q\text{air} = GVF\text{air} * Q\text{mix}$$

$$Q\text{liquid} = (1 - GVF\text{air}) Q\text{mix}$$

Other models and corrections may be used to correct for gas volume fraction.

Other information relating to the gas volume fraction in a fluid and the speed of sound (or sonic velocity) in the fluid, is described in "Fluid Mechanics and Measurements in two-phase flow Systems", Institution of mechanical engineers, proceedings 1969-1970 Vol. 184 part 3C, Sep. 24-25 1969, Birdcage Walk, Westminster, London S.W. 1, England, which is incorporated herein by reference.

FIG. 1 illustrates a schematic drawing of an embodiment of the present invention. The apparatus 10 includes a sensing device 16 comprising an array of pressure sensors (or transducers) 18-21 spaced axially along the outer surface 22 of a pipe 14, having a process flow propagating therein. The pressure sensors measure the unsteady pressures produced by acoustical and vortical disturbances within the pipe, which are indicative of the SOS propagating through the pipe and the velocity of the mixture 12. The output signals ($P_1$-$P_N$) of the pressure sensors 18-21 are provided to the processor 24, which processes the pressure measurement data and determines gas volume fraction (GVF), the uncompensated volumetric flow rate and the compensated volumetric flow rate, as described hereinbefore.

In an embodiment of the present invention shown in FIG. 1, the apparatus 10 has at least four pressure sensors 18-21 disposed axially along the pipe 14 for measuring the unsteady pressure $P_1$-$P_N$ of the mixture 12 flowing therethrough. Both measurements are derive by interpreting the unsteady pressure field within the process piping using multiple transducers displaced axially over ~2 diameters in length. The flow measurements can be performed using ported pressure transducers or clamp-on, strain-based sensors.

The apparatus 10 has the ability to measure the gas volume fraction and volumetric flow rate using one or both of the following techniques described herein below:

1) Determining the speed of sound of acoustical disturbances or sound waves propagating through the flow 12 using the array of pressure sensors 18-21, and/or
2) Determining the velocity of vortical disturbances or "eddies" propagating through the flow 12 using the array of pressure sensors 18-21.

Generally, the first technique measures unsteady pressures created by acoustical disturbances propagating through the flow 12 to determine the speed of sound (SOS) propagating through the flow. Knowing the pressure and/or temperature of the flow and the speed of sound of the acoustical disturbances, the processing unit 24 can determine the gas volume fraction of the mixture, as described and shown in FIG. 3.

The apparatus in FIG. 1 also contemplates providing one or more acoustic sources 27 to enable the measurement of the speed of sound propagating through the flow for instances of acoustically quiet flow. The acoustic sources may be a device that taps on and/or vibrates the wall of the pipe, for example. The acoustic sources may be disposed at the input end of output end of the array of sensors 18-21, or at both ends as shown. One should appreciate that in most instances the acoustics sources are not necessary and the apparatus passively detects the acoustic ridge provided in the flow 12. The passive noise includes noise generated by pumps, valves, motors, and the turbulent mixture itself.

Figure 10:
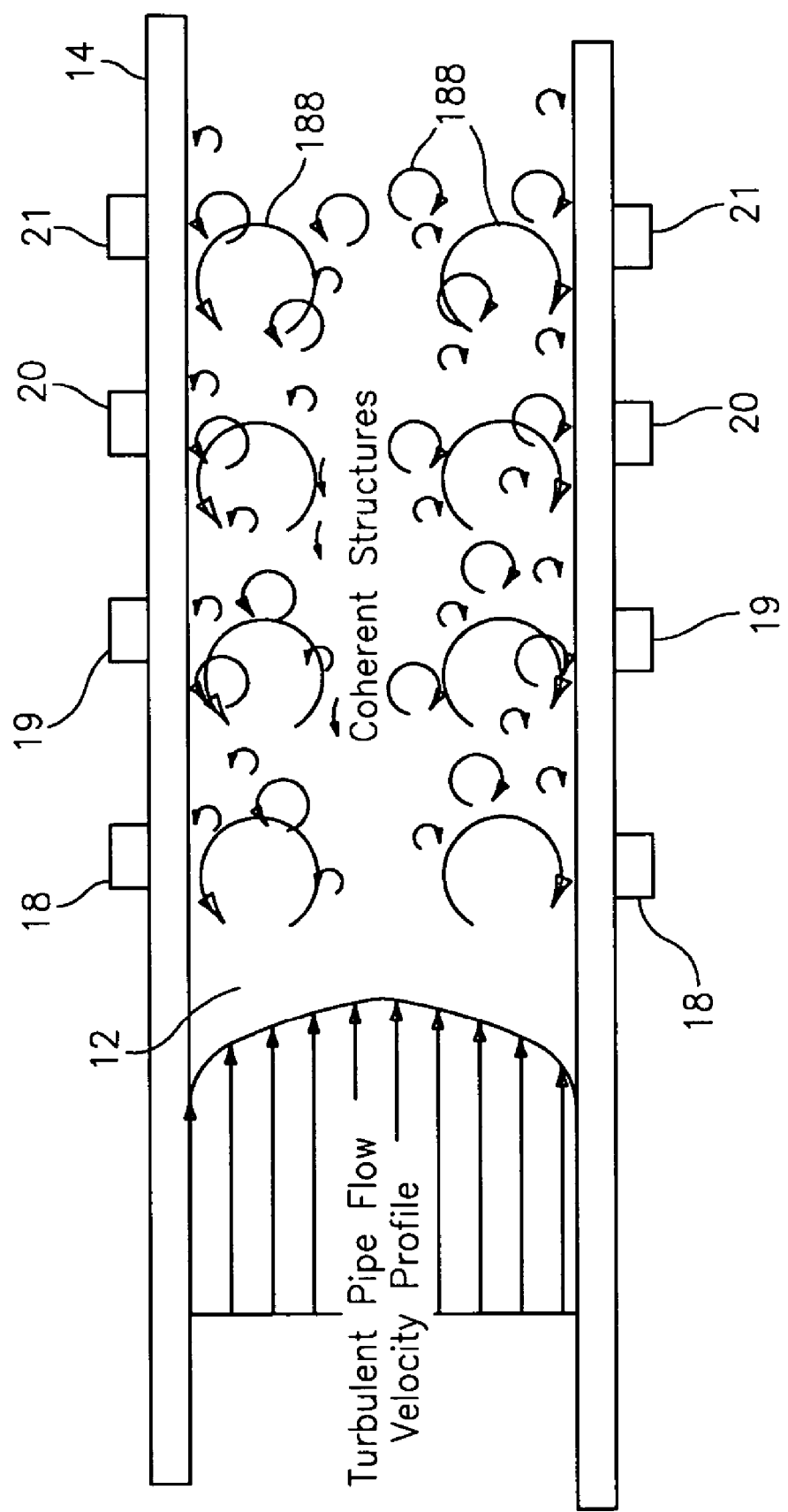
FIG. 10 is a cross-sectional view of a pipe having a turbulent pipe flowing having coherent structures therein, in accordance with the present invention.

The second technique measures the velocities associated with unsteady flow fields and/or pressure disturbances created by vortical disturbances or "eddies" 118 to determine the velocity of the flow 12. The pressure sensors 18-21 measure the unsteady pressures $P_1$-$P_N$ created by the vortical disturbances as these disturbances convect within the flow 12 through the pipe 14 in a known manner, as shown in FIG. 10. Therefore, the velocity of these vortical disturbances is related to the velocity of the mixture and hence the volumetric flow rate may be determined, as will be described in greater detail hereinafter.

In one embodiment of the present invention as shown in FIG. 1, each of the pressure sensors 18-21 may include a piezoelectric film sensor to measure the unsteady pressures of the mixture 12 using either technique described hereinbefore.

The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 14 due to unsteady pressure variations (e.g., vortical and/or acoustical) within the process mixture 12. Strain within the pipe is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,833, publication number 04-0168523, now abandoned, which is incorporated herein by reference.

Figure 4:
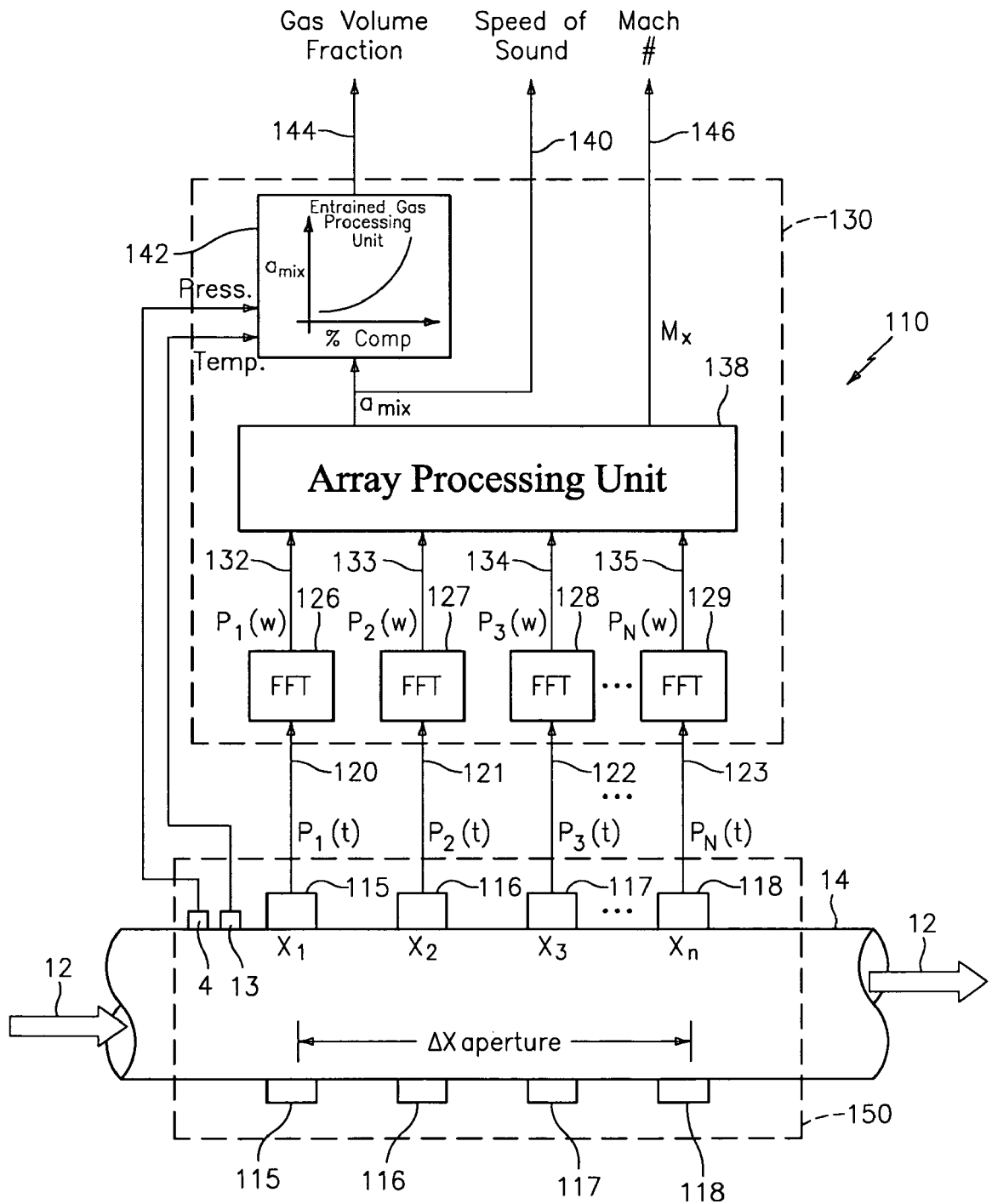
FIG. 4 is a block diagram of an apparatus for measuring the speed of sound propagating through a process flow flowing within a pipe, in accordance with the present invention.

The apparatus 10 of the present invention may be configured and programmed to measure and process the detected unsteady pressures $P_1(t)$-$P_N(t)$ created by acoustic waves and/or vortical disturbances, respectively, propagating through the mixture to determine the SOS within the pipe 14 and the velocity of the mixture 12. One such apparatus 110 is shown in FIG. 4 that measures the speed of sound (SOS) of one-dimensional sound waves propagating through the mixture to determine the gas volume fraction of the mixture. It is known that sound propagates through various mediums at various speeds in such fields as SONAR and RADAR fields. The speed of sound propagating through the pipe and mixture 12 may be determined using a number of known techniques, such as those set forth in U.S. patent application Ser. No. 09/344,094, entitled "Fluid Parameter Measurement in Pipes Using Acoustic Pressures", filed Jun. 25, 1999, now U.S. Pat. No. 6,354,147; U.S. patent application Ser. No. 09/729,994, filed Dec. 4, 2002, now U.S. Pat. No. 6,609,069; U.S. patent application Ser. No. 09/997,221, filed Nov. 28, 2001, now U.S. Pat. No. 6,587,798; and U.S. patent application Ser. No. 10/007,749, entitled "Fluid Parameter Measurement in Pipes Using Acoustic Pressures", filed Nov. 7, 2001, each of which are incorporated herein by reference.

In accordance with the present invention, the speed of sound propagating through the mixture 12 is measured by passively listening to the flow with an array of unsteady pressure sensors to determine the speed at which one-dimensional compression waves propagate through the mixture 12 contained within the pipe 14.

As shown in FIG. 4, an apparatus 110 measuring the speed of sound in the mixture 12 has an array of at least two acoustic pressure sensors 115,116, located at two locations $x_1,x_2$ axially along the pipe 14. One will appreciate that the sensor array may include more than two pressure sensors as depicted by pressure sensors 117,118 at location ,$x_3$, $X_N$. The pressure generated by the acoustic waves may be measured through pressure sensors 115-118. The pressure sensors 115-118 provide pressure time-varying signals $P_1(t),P_2(t),P_3(t),P_N(t)$ on lines 120,121,122,123 to a signal processing unit 130 to known Fast Fourier Transform (FFT) logics 126,127, 128,129, respectively. The FFT logics 126-129 calculate the Fourier transform of the time-based input signals $P_1(t)$-$P_N(t)$ and provide complex frequency domain (or frequency based) signals $P_1(\omega),P_2(\omega),P_3(\omega),P_N(\omega)$ on lines 132,133, 134,135 indicative of the frequency content of the input signals. Instead of FFT's, any other technique for obtaining the frequency domain characteristics of the signals P1(t)-PN(t), may be used. For example, the cross-spectral density and the power spectral density may be used to form a frequency domain transfer functions (or frequency response or ratios) discussed hereinafter.

The frequency signals $P_1(\omega)$-$P_N(\omega)$ are fed to array processing unit 138 which provides a signal to line 140 indicative of the speed of sound of the mixture $a_{mix}$ (discussed more hereinafter). The $a_{mix}$ signal is provided to map (or equation) logic 142, which converts $a_{mix}$ to a percent composition of a mixture and provides a % Comp signal to line 44-144 indicative thereof (as discussed hereinafter).

More specifically, for planar one-dimensional acoustic waves in a homogenous mixture, it is known that the acoustic pressure field P(x,t) at a location x along the pipe 14, where the wavelength λ of the acoustic waves to be measured is long compared to the diameter d of the pipe 14 (i.e., λ/d>>1), may be expressed as a superposition of a right traveling wave and a left traveling wave, as follows:

$$P(x,t)=(Ae^{-ik_r x}+Be^{+ik_l x})e^{i\omega t} \qquad \text{Eq. 1}$$

where A, B are the frequency-based complex amplitudes of the right and left traveling waves, respectively, x is the pressure measurement location along a pipe 14, ω is frequency (in rad/sec, where ω=2πf), and $k_r$, $k_l$ are wave numbers for the right and left traveling waves, respectively, which are defined as:

$$k_r \equiv \left(\frac{\omega}{a_{mix}}\right)\frac{1}{1+M_x} \text{ and } k_l \equiv \left(\frac{\omega}{a_{mix}}\right)\frac{1}{1-M_x} \qquad \text{Eq. 2}$$

where $a_{mix}$ is the speed of sound of the mixture in the pipe, ω is frequency (in rad/sec), and $M_x$ is the axial Mach number of the flow of the mixture within the pipe, where:

$$M_x \equiv \frac{V_{mix}}{a_{mix}} \qquad \text{Eq. 3}$$

where Vmix is the axial velocity of the mixture. For non-homogenous mixtures, the axial Mach number represents the average velocity of the mixture and the low frequency acoustic field description remains substantially unaltered.

The data from the array of sensors 115-118 may be processed in any domain, including the frequency/spatial domain, the temporal/spatial domain, the temporal/wave-number domain or the wave-number/frequency (k-ω) domain. As such, any known array processing technique in any of these or other related domains may be used if desired, similar to the techniques used in the fields of SONAR and RADAR.

Figure 9:
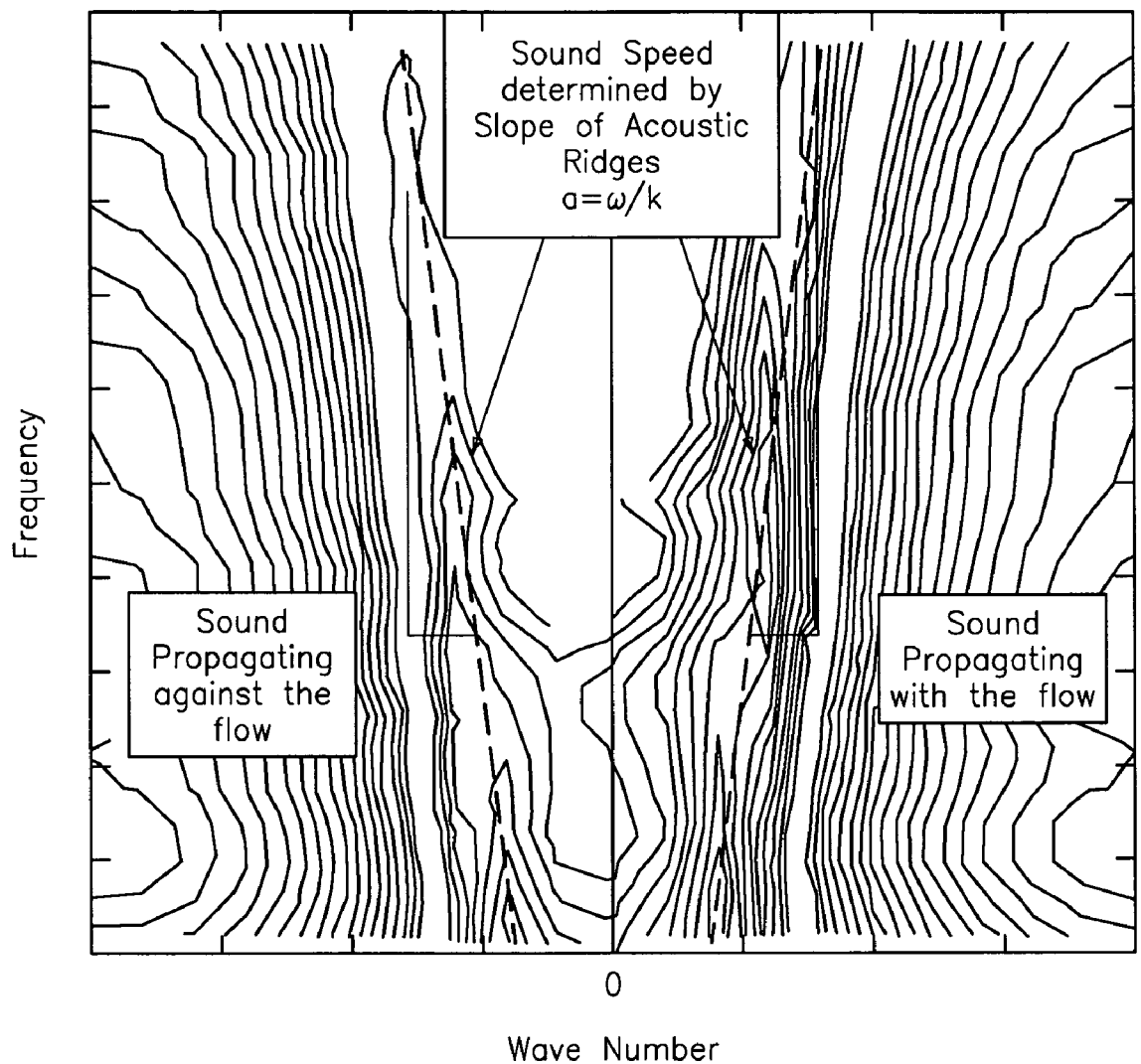
FIG. 9 is a K-w plot for acoustic field within 3 inch pipe containing ~2% air by volume entrained in water flowing 240 gpm, in accordance with the present invention.

One such technique of determining the speed of sound propagating through the flow 12 is using array processing techniques to define an acoustic ridge in the k-ω plane as shown in FIG. 9. The slope of the acoustic ridge is indicative of the speed of sound propagating through the flow 12. This technique is similar to that described in U.S. Pat. No. 6,587,798 filed Nov. 28, 2001, titled "Method and System for Determining The Speed of Sound in a Fluid Within a Conduit", which is incorporated herein by reference. The speed of sound (SOS) is determined by applying sonar arraying processing techniques to determine the speed at which the one dimensional acoustic waves propagate past the axial array of unsteady pressure measurements distributed along the pipe 14.

The signal processor 24 performs a Fast Fourier Transform (FFT) of the time-based pressure signals $P_1(t)$-$P_N(t)$ to convert the pressure signal into the frequency domain. The power of the frequency-domain pressure signals are then determined and defined in the k-ω plane by using array processing algorithms (such as Capon and Music algorithms). The acoustic ridge in the k-ω plane, as shown in the k-ω plot of FIG. 9, is then determined. The speed of sound (SOS) is determined by measuring slope of the acoustic ridge. The gas volume fraction is then calculated or otherwise determined, as described hereinafter.

The flow meter of the present invention uses known array processing techniques, in particular the Minimum Variance, Distortionless Response (MVDR, or Capon technique), to identify pressure fluctuations, which convect with the materials flowing in a conduit and accurately ascertain the velocity, and thus the flow rate, of said material. These processing techniques utilize the covariance between multiple sensors 18-21 at a plurality of frequencies to identify signals that behave according to a given assumed model; in the case of the apparatus 10, a model, which represents pressure variations 20 convecting at a constant speed across the pressure sensors comprising the flow meter monitoring head 12.

To calculate the power in the k-ω plane, as represent by a k-ω plot (see FIG. 9) of either the pressure signals, the processor 58 determines the wavelength and so the (spatial) wavenumber k, and also the (temporal) frequency and so the angular frequency ω, of various spectral components of the acoustic waves created passively or actively within the pipe. There are numerous algorithms available in the public domain to perform the spatial/temporal decomposition of arrays of sensor units 18-21.

In the case of suitable acoustic pressures being present, the power in the k-ω plane shown in a k-ω plot of FIG. 9 so determined will exhibit a structure that is called an acoustic ridge 61 associated with sound propagating with the flow and one associated with sound propagating against the flow. The acoustic ridge represents the concentration of the disturbances that propagate with and against the flow and is a mathematical manifestation of the relationship between the spatial variations and temporal variations described above. Such a plot will indicate a tendency for k-ω pairs to appear more or less along a line with some slope, the slope indicating the speed of sound traveling in both directions, as is described in more detail below. The power in the k-ω plane so determined is then provided to a acoustic ridge identifier, which uses one or another feature extraction method to determine the location and orientation (slope) of any acoustic ridge present in the k-ω plane. Finally, information including the acoustic ridge orientation (slope) is used by an analyzer to determine the speed of sound.

The array processing unit 138 (FIG. 4) uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where λ is the wavelength of a spectral component, and corresponding angular frequencies given by $\omega=2\pi\nu$.

The prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine speed of sound propagating through the fluid 12.

Also, some or all of the functions within the processor 130 may be implemented in software (using a microprocessor or computer) and/or firmware, or may be implemented using analog and/or digital hardware, having sufficient memory, interfaces, and capacity to perform the functions described herein.

It is within the scope of the present invention that the pressure sensor spacing may be known or arbitrary and that as few as two sensors are required if certain information is known about the acoustic properties of the process flow 12. The pressure sensors are spaced sufficiently such that the entire length of the array (aperture) is at least a significant fraction of the measured wavelength of the acoustic waves being measured. The acoustic wavelength is a function of the type or characteristics of flow 12.

Based on the above discussion, one may use a short length scale aperture to measure the sound speed.

The characteristic acoustic length scale is: $\lambda=c/f$; where c is the speed of sound in a mixture, f is frequency and λ is wavelength.

If Aperture=L and if L/λ is approx. constant.
Then Lwater/λwater=Lwater*f/C$_{water}$≈L$_{GVF}$*f/c$_{GVF}$
Therefore: L$_{GVF}$=Lwater (C$_{GVF}$/C$_{water}$); where GVF is gas volume fraction.

Thus for SOS of water (Cwater=5,000 ft/sec), and SOS of the Gas volume fraction (C GVF=500 ft/sec) and a length aperture of L water=5 ft (which we have shown is sufficient to accurately measure the SOS of water), the length aperture for a gas volume fraction L$_{GVF}$ would be about 0.5 feet.

The entrained gas processing unit 142 (FIG. 4) assumes a nearly isothermal condition for the flow 12. As such the gas volume fraction or the void fraction is related to the speed of sound by the following quadratic equation:

$$Ax^2+Bx+C=0$$

wherein x is the speed of sound, A=1+rg/rl*(K$_{eff}$P-1)-K$_{eff}$/P, B=K$_{eff}$/P-2+rg/rl; C=1-K$_{eff}$/rl*a$_{meas}$^2); Rg=gas density, rl=liquid density, K$_{eff}$=effective K (modulus of the liquid and pipewall), P=pressure, and a$_{meas}$=measured speed of sound.

Effectively, $$\text{Gas Volume Fraction (GVF)}=(-B+\text{sqrt}(B^2-4*A*C))/(2*A)$$

Alternatively, the sound speed of a mixture can be related to volumetric phase fraction ($\phi_i$) of the components and the sound speed (a) and densities (ρ) of the component through the Wood equation.

$$\frac{1}{\rho_{mix}a_{mix\infty}^2}=\sum_{i=1}^{N}\frac{\phi_i}{\rho_i a_i^2} \text{ where } \rho_{mix}=\sum_{i=1}^{N}\rho_i\phi_i$$

One dimensional compression waves propagating within a mixture 12 contained within a pipe 14 exert an unsteady internal pressure loading on the pipe. The degree to which the pipe displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity (a$_{eff}$) for one dimensional compression is given by the following expression:

$$a_{eff}=\frac{1}{\sqrt{\frac{1}{a_{mix\infty}^2}+\rho_{mix}\frac{2R}{Et}}} \quad (\text{eq 1})$$

Note: "vacuum backed" as used herein refers to a situation in which the fluid surrounding the pipe externally has negligible acoustic impedance compared to that of the mixture internal to the pipe 14. For example, meter containing a typical water and pulp slurry immersed in air at standard atmospheric conditions satisfies this condition and can be considered "vacuum-backed".

Figure 5:
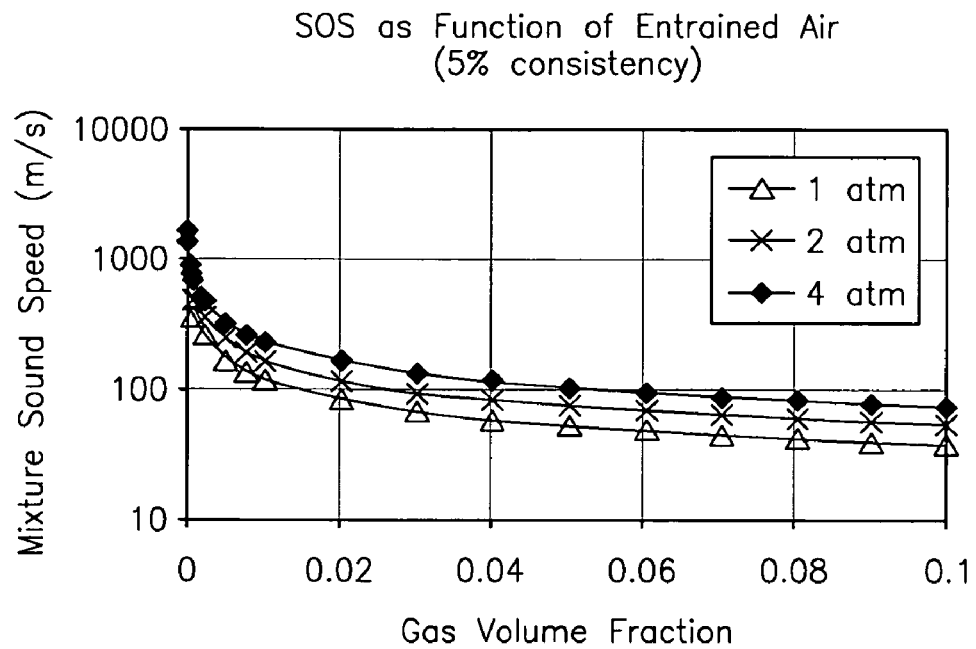
FIG. 5 is a plot of Mixture Sound Speed as a function of gas volume fraction for a 5% consistency slurry over a range of process pressures, in accordance with the present invention.

The mixing rule essentially states that the compressibility of a mixture (1/(ρ a²)) is the volumetrically-weighted average of the compressibilities of the components. For gas/liquid mixtures 12 at pressure and temperatures typical of paper and pulp industry, the compressibility of gas phase is orders of magnitudes greater than that of the liquid. Thus, the compressibility of the gas phase and the density of the liquid phase primarily determine mixture sound speed., and as such, it is necessary to have a good estimate of process pressure to interpret mixture sound speed in terms of volumetric fraction of entrained air. The effect of process pressure on the relationship between sound speed and entrained air volume fraction is shown in FIG. 5.

Figure 6:
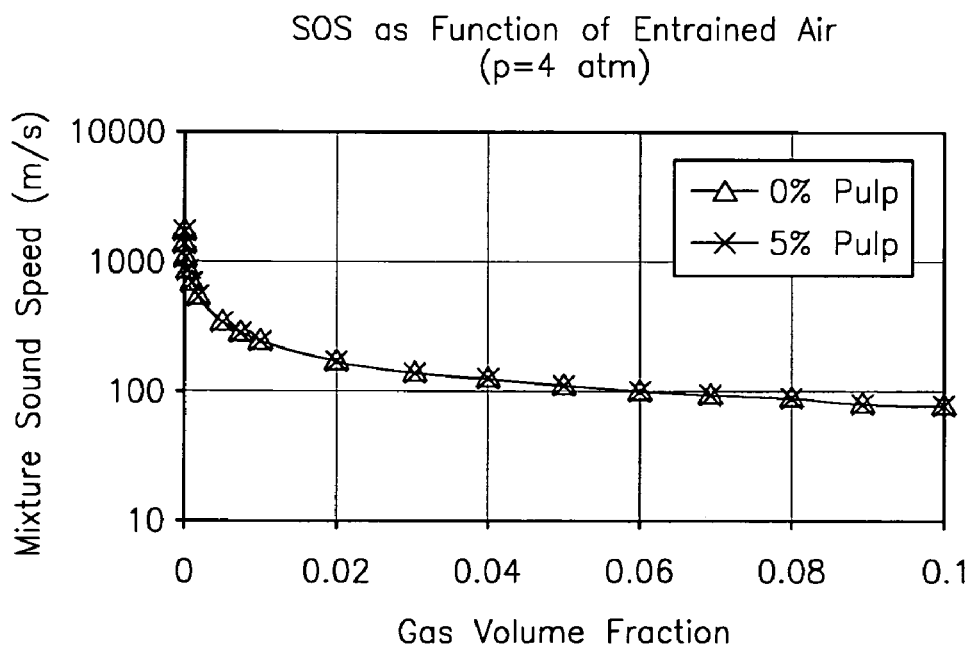
FIG. 6 is a plot of Mixture Sound Speed a function of gas volume fraction for pure water and a 5% consistency slurry at 4 atm process pressure, in accordance with the present invention.

Conversely, however, detailed knowledge of the liquid/slurry is not required for entrained air measurement. Variations in liquid density and compressibility with changes in consistency have a negligible effect on mixture sound speed compared to the presence of entrained air. FIG. 6 shows the mixture sound speed as a function of entrained air volume fraction for two slurries, one with 0% wood fiber and the other with 5% wood fiber by volume. As shown, the relationship between mixture sound speed and gas volume fraction is essentially indistinguishable for the two slurries. Furthermore, mixture sound speed is shown to an excellent indicator of gas volume fraction, especially for the trace to moderate amounts of entrained air, from 0 to 5% by volume, typically encountered in the paper and pulp industry.

For paper and pulp slurries, the conditions are such that for slurries with non-negligible amounts of entrained gas, say <0.01%, the compliance of standard industrial piping (Schedule 10 or 40 steel pipe) is typically negligible compared to that of the entrained air.

Figure 7:
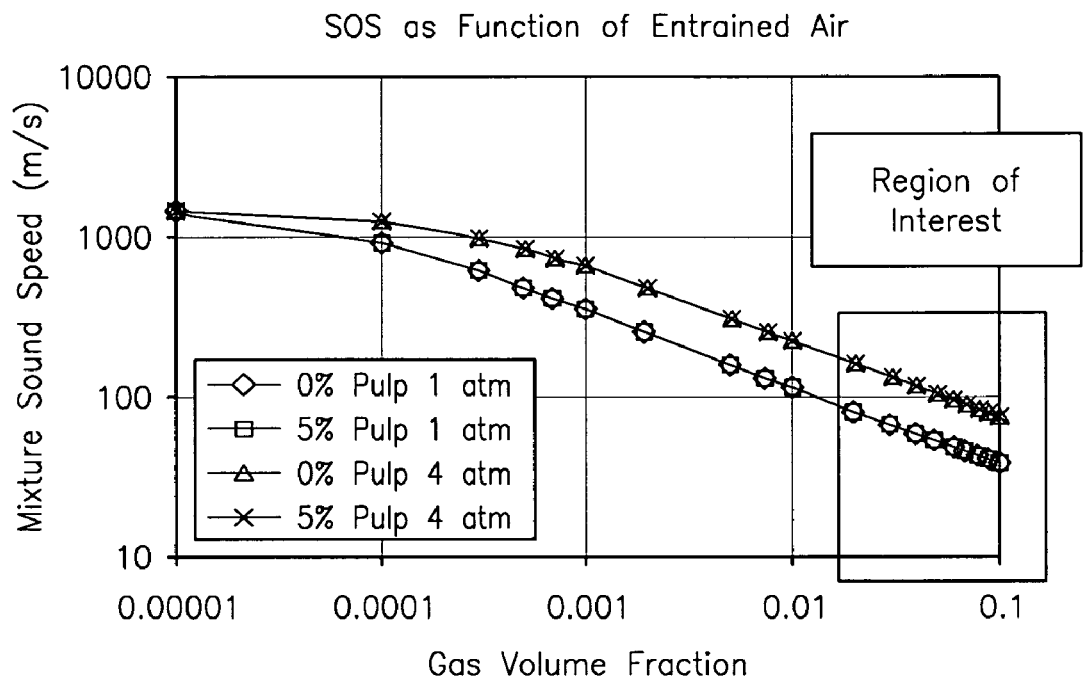
FIG. 7 is a plot of Mixture Sound Speed as a function of gas volume fraction for different consistency slurry over a range of process pressures, in accordance with the present invention.
Figure 8:
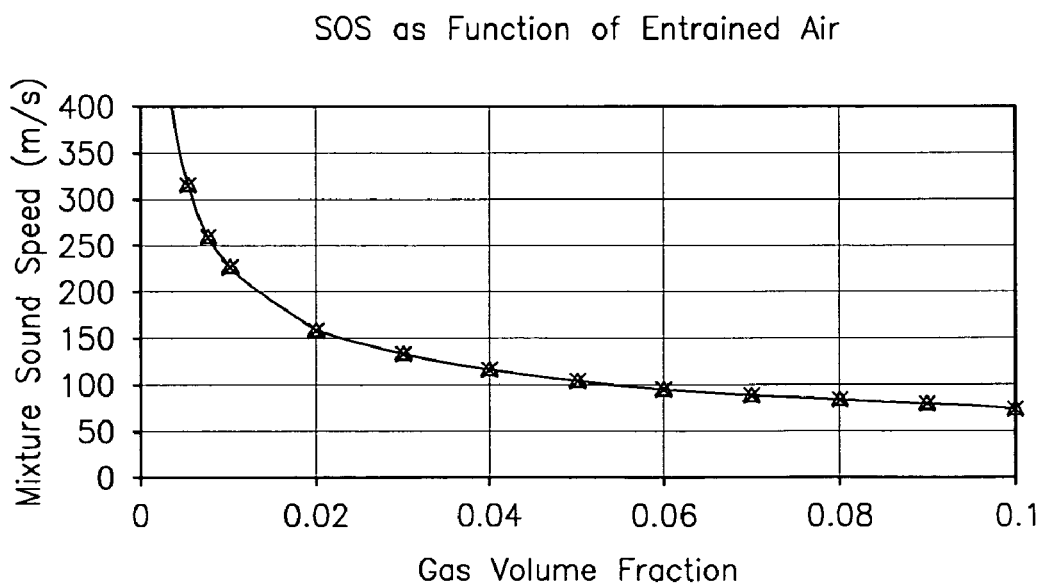
FIG. 8 is a plot of Mixture Sound Speed a function of entrained air volume fraction for slurry at a process pressure, in accordance with the present invention.

FIGS. 7 and 8 above show the relationship between sound speed and entrained air for slurries 12 with pulp contents representative of the range used in the paper and pulp industry. Referring to FIG. 7, two slurry consistencies are shown; representing the lower limit, a pure water mixture is considered, and representing the higher end of consistencies, a 5% pulp/95% water slurry is considered. Since the effect of entrained air on the sound speed of the mixture is highly sensitive to the compressibility of the entrained air, the effect of the entrained air is examined at two pressures, one at ambient representing the lower limit of pressure, and one at 4 atmospheres representing a typical line pressure in a paper process. As shown, the consistency of the liquid slurry 12, i.e., the pulp content, has little effect on the relationship between entrained air volume fraction and mixture sound speed. This indicates that an entrained air measurement could be accurately performed, within 0.01% or so, with little or no knowledge of the consistency of the slurry. The chart does show a strong dependence on line pressure. Physically, this effect is linked to the compressibility of the air, and thus, this indicates that reasonable estimates of line pressure and temperature would be required to accurately interpret mixture sound speed in terms of entrained air gas volume fraction.

FIG. 7 also shows that for the region of interest, from roughly 1% entrained air to roughly 5% entrained air, mixture sound speeds (amix) are quite low compare to the liquid-only sound speeds. In this example, the sound speed of the pure water and the 5% pulp slurry were calculated, based on reasonable estimates of the constituent densities and compressibilities, to be 1524 m/s and 1541 m/s, respectively. The sound speed of these mixtures with 1% to 5% entrained air at typical operating pressure (1 atm to 4 atms) are on the order of 100 m/sec. The implication of these low sound speed is that the mixture sound speed could be accurately determined with a array of sensors, ie using the methodology described in aforementioned U.S. Pat. No. 6,354,147, and/or U.S. Pat. No. 6,732,575, with an aperture that is similar, or identical, to an array of sensors that would be suitable to determine the convection velocity, using the methodology described in aforementioned U.S. Pat. No. 6,889,562, which is incorporated herein by reference. Thus, performing a volumetric flow measurement and an entrained air volumetric flow measurement using the convection velocity and mixture sound speed simultaneously, with the same sensor array would provide functionality currently unavailable to the paper and pulp industry.

For the sound speed measurement, the apparatus 110 utilizes similar processing algorithms as those employed for the volumetric flow measurement. As with convective disturbances (which is described in greater detail hereinafter), the temporal and spatial frequency content of sound propagating within the process piping is related through a dispersion relationship.

$$k = \frac{\omega}{a_{mix}}$$

As before, k is the wave number, defined as $k=2\pi/\lambda$, $\omega$ is the temporal frequency in rad/sec, and $a_{mix}$ is the speed at which sound propagates within the process piping. Unlike disturbances, which convect with the flow, however, sound generally propagates in both directions, with and against the mean flow. For these cases, the acoustic power is located along two acoustic ridges, one for the sound traveling with the flow at a speed of $a_{mix}+V_{mix}$ and one for the sound traveling against the flow at a speed of $a_{mix}-V_{mix}$.

FIG. 9 shows a k-$\omega$ plot generated for acoustic sound field recorded from water flowing at a rate of 240 gpm containing ~2% entrained air by volume in a 3 in, schedule 10, stainless steel pipe. The k-$\omega$ plot was constructed using data from an array of strain-based sensors attached to the outside of the pipe. Two acoustic ridges are clearly evident. Based on the slopes of the acoustic ridges, the sound speed for this for this mixture was 330 ft/sec (100 m/s), consistent with that predicted by the Wood equation. Note that adding 2% air by volume reduces the sound speed of the bubbly mixture to less than 10% of the the sound speed of single phase water.

While the sonar-based flow meter using an array of sensors to measure the speed of sound of an acoustic wave propagating through the mixture, one will appreciate that any means for measuring the speed of sound of the acoustic wave may be used to determine the entrained air volume fraction of the mixture/fluid.

The apparatus 110 further includes the ability to measure of volumetric flow rate of the mixture by comparing the difference of the speed of one dimensional sound waves propagating with and against the mean flow.

This method of determining the volumetric flow rate of the flow 12 relies on the interaction of the mean flow with the acoustic pressure field. The interaction results in sound waves propagating with the mean flow traveling at the speed of sound (if the vapor/liquid mixture were not flowing) plus the convection velocity and, conversely, sound waves traveling against the mean flow propagating at the speed of sound minus the convection velocity. That is, $$a_R = a_{mix} + u$$

$$a_L = a_{mix} - u$$

where $a_R$=velocity of a right traveling acoustic wave relative to a stationary observer (i.e. the pipe 14), $a_L$=velocity of a left traveling acoustic wave apparent to a stationary observer, $a_{mix}$=speed of sound traveling through the mixture (if the mixture was not flowing) and u=the mean flow velocity (assumed to be flowing from left to right in this instance). Combining these two equations yields an equation for the mean velocity, $$u = \frac{a_R - a_L}{2}$$

Therefore, by measuring the propagation velocity of acoustic waves in both directions relative to the pipe 14 as described hereinbefore, the mean flow velocity can be calculated by multiplying the mean flow velocity by the cross-sectional area of the pipe 14.

Further, FIG. 9 illustrates the ability of the present invention to determine the velocity of a fluid moving in a pipe. The color contours represent the relative signal power at all combinations of frequency and wavenumber. The highest power "ridges" represent the acoustic wave with slope of the ridges equal to the propagation speed. The dashed lines show the best-fit two-variable maximization of the power with the two variables being sound speed and flow velocity. The right-side ridge represents the acoustic wave traveling in the same direction as the bulk flow and therefore its slope is steeper than the left-side ridge that represents the acoustic wave traveling in the opposite direction of the flow. This indicates that the acoustic wave traveling in the same direction of the flow is traveling faster than the acoustic wave traveling in the opposite direction of the flow relative to the stationary sensors located on the probe.

As discussed hereinbefore, the apparatus 10 of FIG. 1 embodying the present invention also includes the ability to measure volumetric flow rate of the mixture by measuring the unsteady pressures generated by vortical disturbances 188 propagating in the mixture 12 (see FIG. 10). The apparatus 10 uses one or both of the following techniques to determine the convection velocity of the vortical disturbances within the process flow 12 by:

1) Characterizing the convective ridge of the vortical disturbances using an array of unsteady pressure sensors.
2) Cross-correlating unsteady pressure variations using an array of unsteady pressure sensors.

To measure volumetric flow, the sonar meter characterizes speed at which coherent vortical structures convect past an axial array of sensors using beam forming techniques developed over several decades for underwater acoustic application. Coherent structures are an inherent feature of turbulent boundary layers present in all turbulent flows. Unlike conventional vortex shedding meters, no internal geometry is required to generate these structures.

The overwhelming majority of industrial process flows involve turbulent flow 12. Turbulent fluctuations within the process flow govern many of the flow properties of practical interest including the pressure drop, heat transfer, and mixing. For engineering applications, considering only the time-averaged properties of turbulent flows is often sufficient for design purposes. For sonar based array processing flow metering technology, understanding the time-averaged velocity profile in turbulent flow 12 provides a means to interpret the relationship between speed at which coherent structures 118 convect and the volumetrically averaged flow rate.

Turbulent pipe flows 12 are highly complex flows. Predicting the details of any turbulent flow is problematic, however, much is known regarding the statistical properties of the flow. For instance, turbulent flows contain self-generating, coherent vortical structures often termed "turbulent eddies". The maximum length scale of these eddies is set by the diameter of the pipe 14. These structures remain coherent for several tube diameters downstream, eventually breaking down into progressively smaller eddies until the energy is dissipated by viscous effects.

Experimental investigations have established that eddies generated within turbulent boundary layers convect at roughly 80% of maximum flow velocity. For pipe flows, this implies that turbulent eddies will convect at approximately the volumetrically averaged flow velocity within the pipe 14. The precise relationship between the convection speed of turbulent eddies and the flow rate for each class of meters can be calibrated empirically as described below.

FIG. 10 illustrates the relevant flow features of turbulent pipe flow 12 along with a axial array of sensors 18-21. As shown, the time-averaged axial velocity is a function of radial position, from zero the wall to a maximum at the centerline of the pipe. The flow 12 near the wall is characterized by steep velocity gradients and transitions to relatively uniform core flow near the center of the pipe 14. Vortical structures, often termed turbulent eddies, are superimposed over time averaged velocity profile. These coherent structures contain temporally and spatially random fluctuations with magnitudes typically less than 10% percent of the mean flow velocity and are carried along with the mean flow. Experimental investigations have established that eddies generated within turbulent boundary layers remain coherent for several pipe diameters and convect at roughly 80% of maximum flow velocity (Schlichting, 1979).

From a volumetric flow measurement perspective, the volumetrically averaged flow velocity is of interest. The volumetrically averaged flow velocity, defined as the total volumetric flow rate, Q, divided by the cross sectional area of the conduit, A, is a useful, but arbitrarily defined property of the flow. In fact, given the velocity profile within the pipe, little flow is actually moving at this speed. The precise relationship between the convection speed of turbulent eddies and the flow rate is determined experimentally through calibration for each.

The Reynolds number (Re), based on pipe diameter (D), characterizes many of the engineering properties of the flow. The Reynolds number is a non-dimensional ratio representing the relative importance of inertial forces to viscous forces within a flow:

$$Re = \frac{\text{inertial}}{\text{viscous}} \text{forces} = \frac{\rho u \frac{\partial u}{\partial x}}{\mu \frac{\partial^2 u}{\partial y^2}} = \frac{UD}{v}$$

Where $\rho$ is the fluid density, $\mu$ is the dynamic viscosity, U is the volumetrically averaged flow velocity and $v(=\mu/\rho)$ is the kinematic viscosity.

The critical Reynolds number for pipe flows, above which flows are considered turbulent, is ~2300. Most flows in the paper and pulp industry have Reynolds number ranging from one hundred thousand to several million, well within the turbulent regime. In addition to demarcating a boundary between laminar and turbulent flow regimes, the Reynolds number is a similarity parameter for pipe flows, i.e. flows in geometrically similar pipes with the same Reynolds number are dynamically similar (Schlichting p. 12).

The first technique of determining the convection velocity of the vortical disturbances within the flow 12 is by characterizing the convective ridge of the vortical disturbances using an array of unsteady pressure sensors, similar to that shown in U.S. patent application Ser. No. 09/729,994, filed Dec. 4, 2000, entitled "Method and Apparatus for Determining the Flow Velocity Within a Pipe", which is incorporated herein by reference.

The sonar flow metering methodology uses the convection velocity of coherent structure with turbulent pipe flows 12 to determine the volumetric flow rate. The convection velocity of these eddies 188 is determined by applying sonar arraying processing techniques to determine the speed at which the eddies convect past an axial array of unsteady pressure measurements distributed along the pipe 14, similar to the technique described for the apparatus 110 of FIG. 4 for measuring gas volume fraction with a fluid.

The sonar-based algorithms determine the speed of the eddies 188 by characterizing both the temporal and spatially frequency characteristics of the flow field. For a series of coherent eddies convecting past a fixed array of sensors, the temporal and spatial frequency content of pressure fluctuations are related through the following relationship:

$$k = \frac{\omega}{U_{convect}}$$

Here k is the wave number, defined as $k=2\pi/\lambda$ and has units of 1/length, $\omega$ is the temporal frequency in rad/sec, and $U_{convect}$ is the convection velocity. Thus, the shorter the wavelength (larger k) is, the higher the temporal frequency.

In sonar array processing, the spatial/temporal frequency content of time stationary sound fields are often displayed using "k-$\omega$ plots", as discussed hereinbefore. K-$\omega$ plots are essentially three-dimensional power spectra in which the power of a sound field is decomposed into bins corresponding to specific spatial wave numbers and temporal frequencies. On a k-$\omega$ plot, the power associated with a pressure field convecting with the flow is distributed in regions, which satisfies the dispersion relationship developed above. This region is termed "the convective ridge" 201 (Beranek, 1992) and the slope of this ridge on a k-w plot indicates the convective velocity of the pressure field. This suggests that the convective velocity of turbulent eddies, and hence flow rate within a pipe 14, can be determined by constructing a k-$\omega$ plot from the output of a phased array of sensor and identifying the slope of the convective ridge 201.

Figure 12:
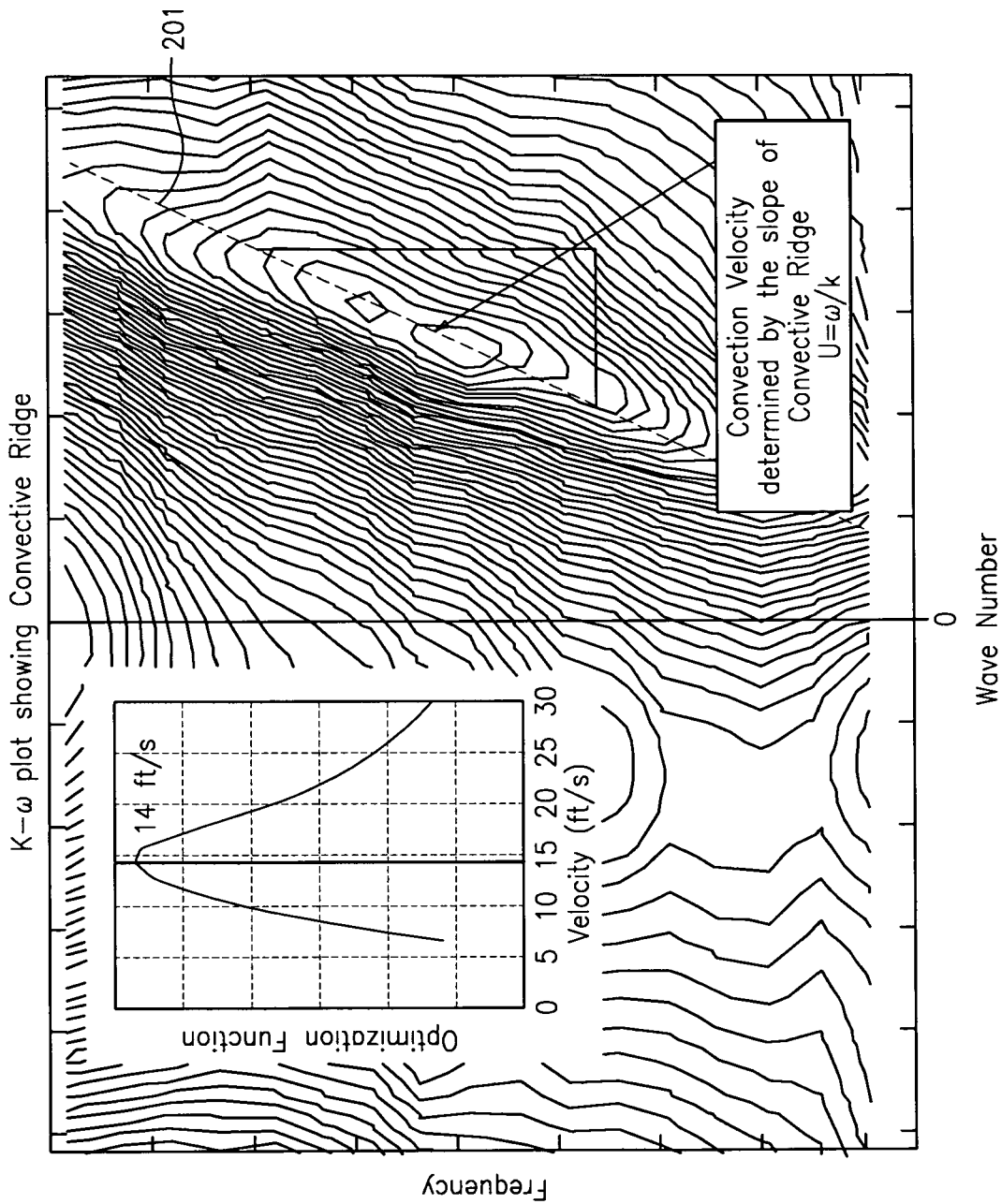
FIG. 12 a kω plot of data processed from an apparatus embodying the present invention that illustrates slope of the convective ridge, and a plot of the optimization function of the convective ridge, in accordance with the present invention.

FIG. 12 shows an example of a k-$\omega$ plot generated from a phased array of pressure sensors. The power contours show a well-defined convective ridge. A parametric optimization method was used to determine the "best" line representing the slope of the convective ridge 201. For this case, a slope of 14.2 ft/sec was determined. The intermediate result of the optimization procedure is displayed in the insert, showing that optimized value is a unique and well-defined optima.

The k-$\omega$ plot shown in FIG. 12 illustrates the fundamental principle behind sonar based flow measure, namely that axial arrays of pressure sensors can be used in conjunction with sonar processing techniques to determine the speed at which naturally occurring turbulent eddies convect within a pipe.

Figure 11:
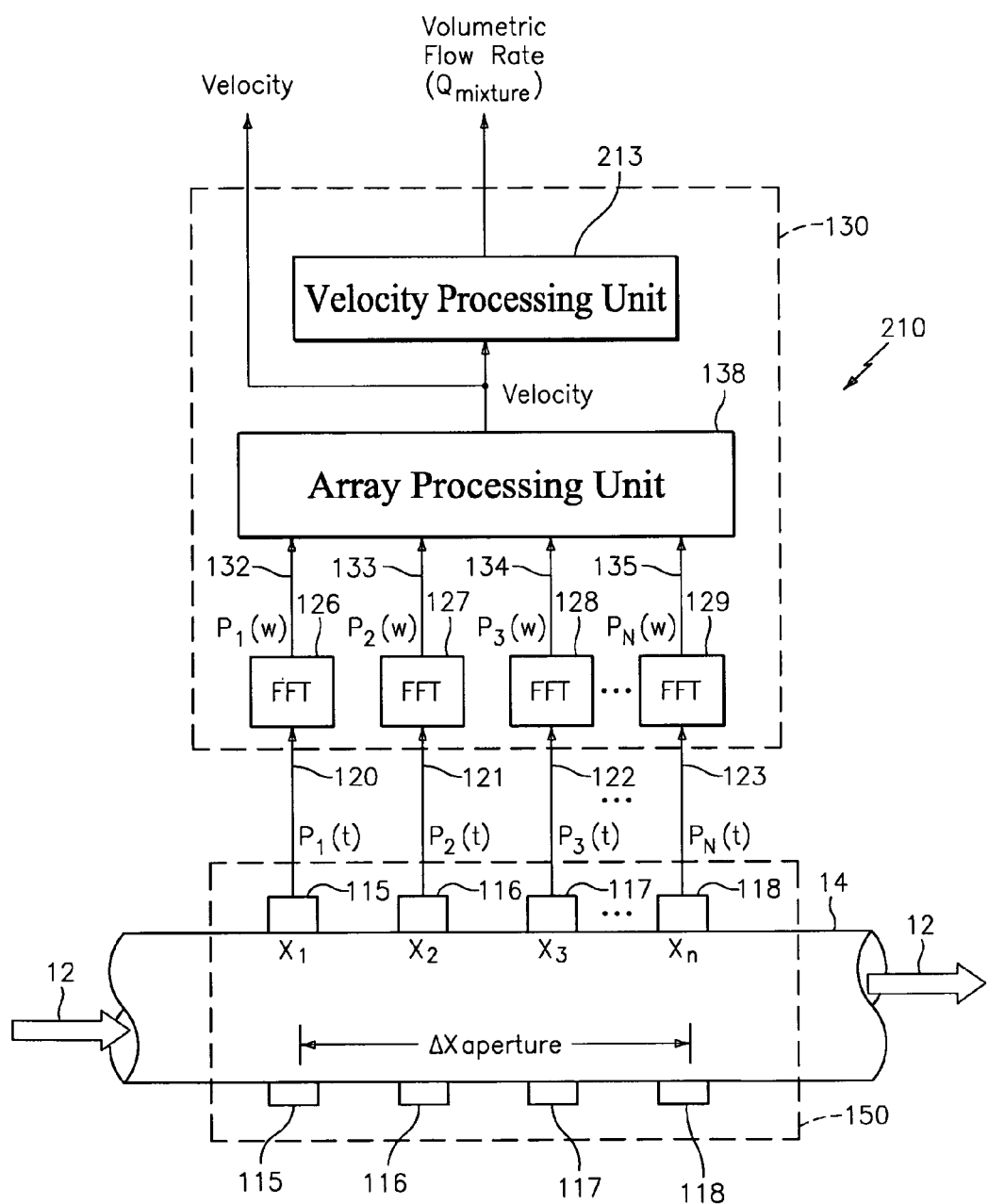
FIG. 11 is a block diagram of an apparatus for measuring the vortical field of a process flow within a pipe, in accordance with the present invention.

As shown in FIG. 11, the array processing unit 138 of the flow meter 210 processes the input pressure signals $P_1(\omega)$-$P_N(\omega)$ to define the convective ridge 201 (see FIG. 12) in the k-$\omega$ plane. The slope of the ridge determines the velocity of the aerated fluid or mixture 12. A velocity processing determines the volumetric flow rate of the aerated fluid 12 using the relationship of:

Volumetric Flow Rate=Velocity (Cross-sectional Area of Pipe).

Figure 13:
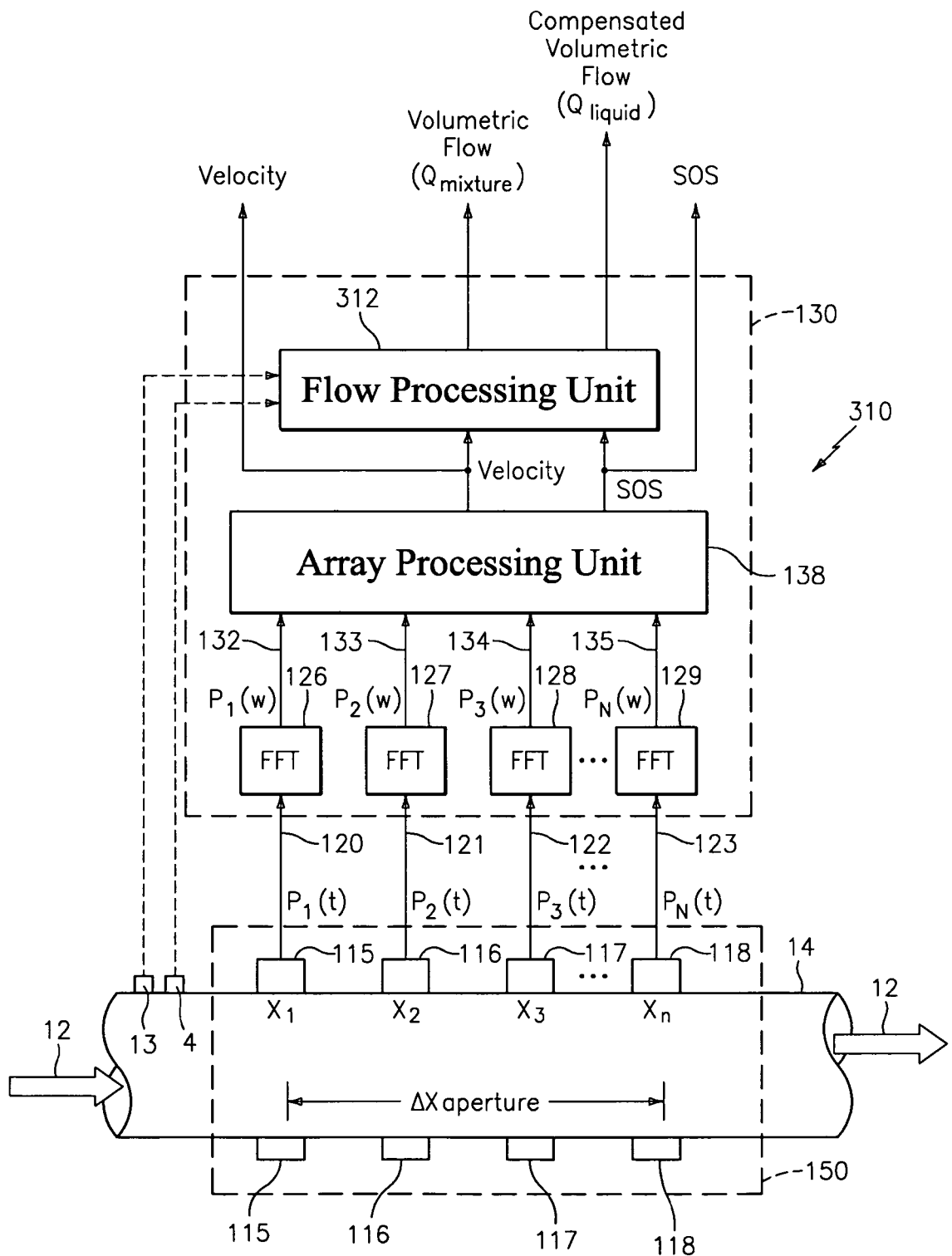
FIG. 13 is a block diagram of an apparatus for measuring the vortical field and acoustic field of a process flow within a pipe, in accordance with the present invention.

While two separate apparatus 110 and 210 may be used to measure the gas volume fraction and velocity, respectively, of the fluid having entrained gas therein to determine the compensated volumetric flow rate, the present invention contemplates a single array of sensors and processing unit may be used to perform both functions as suggested hereinbefore. Such an apparatus 310 is shown in FIG. 13, wherein a single array of pressure sensors 115-118 is used to determine both the speed of sound within the fluid and the velocity of the fluid. A flow processing unit 312 that combines the functionality of the entrained air processing unit 142 of FIG. 4 and the velocity processing unit 213 of FIG. 11 to provide a compensated volumetric flow measurement.

The present invention shown in FIGS. 1, 4, 11 and 13 contemplate that output signals P1( )-PN( ) of adjacent signals may be differenced to filter out common mode noise or acoustics to provide spatial filtering. Also, while the present invention shows an apparatus having two to four sensors to form an array, the present invention contemplates that array may includes any number of sensors, for example, arrays having between 2 and sixteen sensors.

Figure 14:
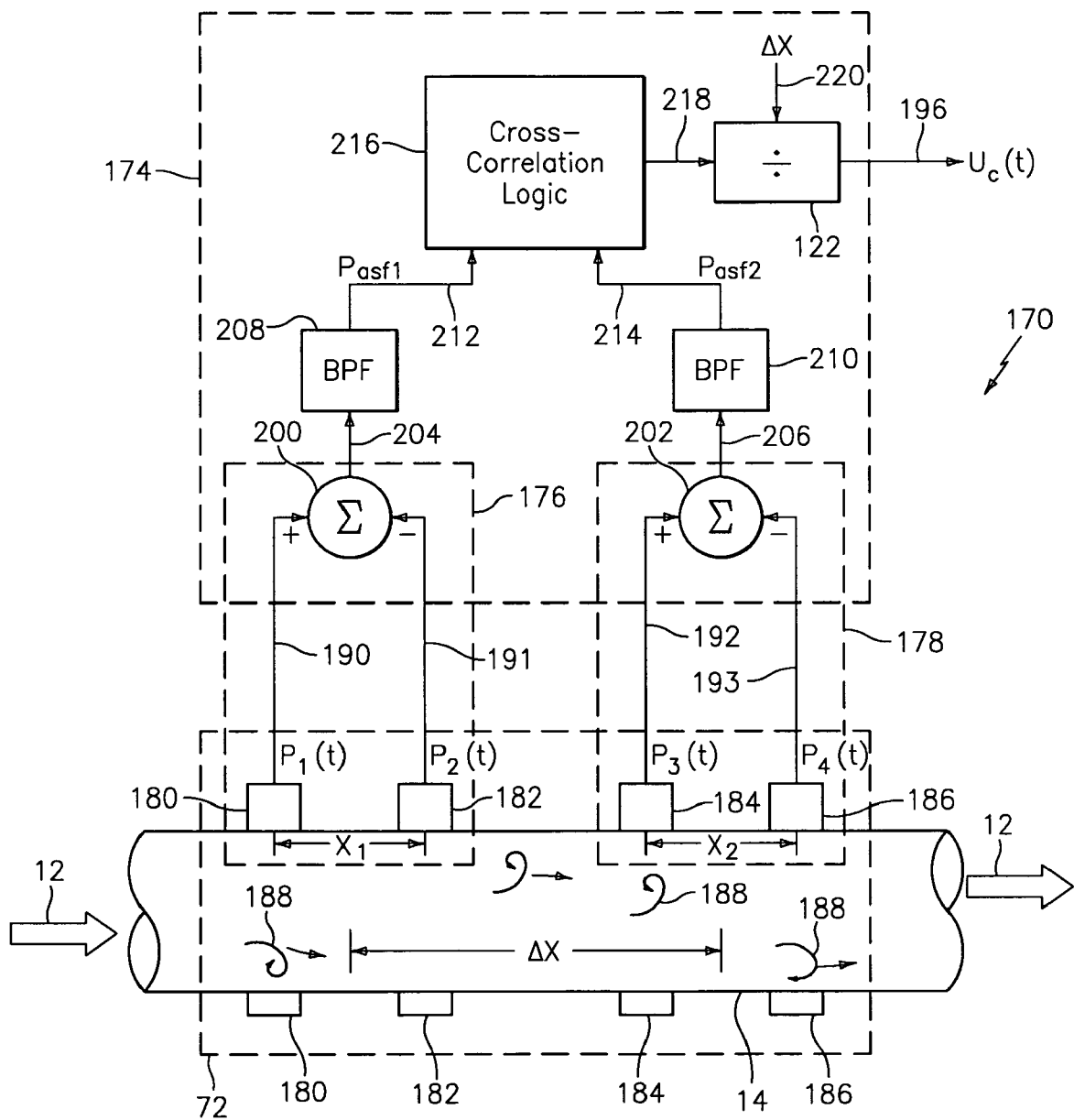
FIG. 14 is a block diagram of another apparatus for measuring the vortical field of a process flow within a pipe, in accordance with the present invention.
Figure 15:
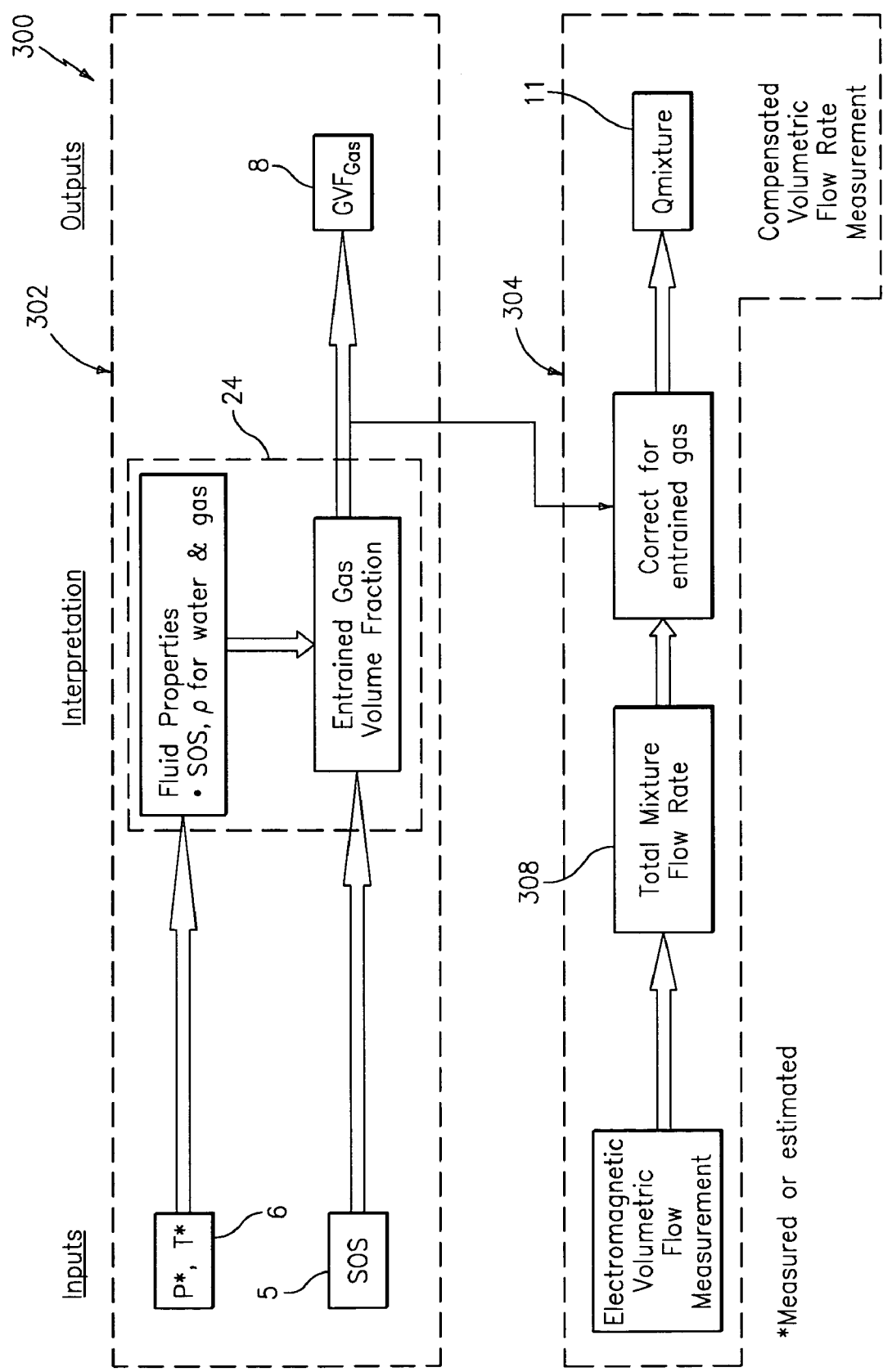
FIG. 15 is a functional flow diagram of an apparatus embodying the present invention that compensates the volumetric flow measurement of an electromagnetic flow meter, in accordance with the present invention.

In the second technique, the apparatus 170 of FIG. 14 determines the convection velocity of the vortical disturbances within the flow by cross correlating unsteady pressure variations using an array of unsteady pressure sensors, similar to that shown in U.S. patent application Ser. No. 10/007,736, filed Nov. 8, 2001, entitled "Flow Rate Measurement Using Unsteady Pressures", which is incorporated herein by reference.

Referring to FIG. 14, the apparatus 170 includes a sensing section 72 along a pipe 14 and a signal processing unit 174. The pipe 14 has two measurement regions 176,178 located a distance $\Delta X$ apart along the pipe 14. At the first measurement region 176 are two unsteady (or dynamic or ac) pressure sensors 180,182, located a distance $X_1$ apart, capable of measuring the unsteady pressure in the pipe 14, and at the second measurement region 178, are two other unsteady pressure sensors 184,186 located a distance $X_2$ apart, capable of measuring the unsteady pressure in the pipe 14. Each pair of pressure sensors 180,182 and 184,186 act as spatial filters to remove certain acoustic signals from the unsteady pressure signals, and the distances $X_1,X_2$ are determined by the desired filtering characteristic for each spatial filter, as discussed hereinafter.

The apparatus 170 of the present invention measures velocities associated with unsteady flow fields and/or pressure disturbances represented by 188 associated therewith relating to turbulent eddies (or vortical flow fields), inhomogeneities in the flow, or any other properties of the flow, liquid, vapor, or pressure, having time varying or stochastic properties that are manifested at least in part in the form of unsteady pressures. The vortical flow fields are generated within the flow of the pipe 14 by a variety of non-discrete sources such as remote machinery, pumps, valves, elbows, as well as the fluid or mixture flow itself It is this last source, the fluid flowing within the pipe, that is a generic source of vortical flow fields primarily caused by the shear forces between the flow 12 and the wall of the tube that assures a minimum level of disturbances for which the present invention takes unique advantage. The flow generated vortical flow fields generally increase with mean flow velocity and do not occur at any predeterminable frequency. As such, no external discrete vortex-generating source is required within the present invention and thus may operate using passive detection. It is within the scope of the present invention that the pressure sensor spacing may be known or arbitrary and that as few as two sensors are required if certain information is known about the acoustic properties of the system as will be more fully described herein below.

The vortical flow fields 188 are, in general, comprised of pressure disturbances having a wide variation in length scales and which have a variety of coherence length scales such as that described in the reference "Sound and Sources of Sound", A. P. Dowling et al, Halsted Press, 1983, which is incorporated by reference to the extend of understanding the invention. Certain of these vortical flow fields 188 convect at or near, or related to the mean velocity of at least one of the elements within a mixture flowing through the pipe 14. The vortical pressure disturbances 188 that contain information regarding convection velocity have temporal and spatial length scales as well as coherence length scales that differ from other disturbances in the flow. The present invention utilizes these properties to preferentially select disturbances of a desired axial length scale and coherence length scale as will be more fully described hereinafter. For illustrative purposes, the terms vortical flow field and vortical pressure field will be used to describe the above-described group of unsteady pressure fields having temporal and spatial length and coherence scales described herein.

Also, some or all of the functions within the signal processing unit 174 may be implemented in software (using a microprocessor or computer) and/or firmware, or may be implemented using analog and/or digital hardware, having sufficient memory, interfaces, and capacity to perform the functions described herein.

In particular, in the processing unit 174, the pressure signal $P_1(t)$ on the line 190 is provided to a positive input of a summer 200 and the pressure signal $P_2(t)$ on the line 191 is provided to a negative input of the summer 200. The output of the summer 200 is provided to line 204 indicative of the difference between the two pressure signals $P_1$, $P_2$ (e.g., $P_1-P_2=P_{as1}$).

The pressure sensors 180, 182 together with the summer 200 create a spatial filter 176. The line 204 is fed to bandpass filter 208, which passes a predetermined passband of frequencies and attenuates frequencies outside the passband. In accordance with the present invention, the passband of the filter 208 is set to filter out (or attenuate) the dc portion and the high frequency portion of the input signals and to pass the frequencies therebetween. Other passbands may be used in other embodiments, if desired. Passband filter 208 provides a filtered signal $P_{asf}1$ on a line 212 to Cross-Correlation Logic 216, described hereinafter.

The pressure signal $P_3(t)$ on the line 192 is provided to a positive input of a summer 202 and the pressure signal $P_4(t)$ on the line 193 is provided to a negative input of the summer 202. The pressure sensors 183,184 together with the summer 202 create a spatial filter 178. The output of the summer 202 is provided on a line 206 indicative of the difference between the two pressure signals $P_3, P_4$ (e.g., $P_3-P_4=P_{as2}$). The line 206 is fed to a bandpass filter 210, similar to the bandpass filter 108 discussed hereinbefore, which passes frequencies within the passband and attenuates frequencies outside the passband. The filter 210 provides a filtered signal $P_{asf}2$ on a line 214 to the Cross-Correlation Logic 216. The signs on the summers 200,202 may be swapped if desired, provided the signs of both summers are swapped together. In addition, the pressure signals $P_1,P_2,P_3,P_4$ may be scaled prior to presentation to the summers 200,202.

The Cross-Correlation Logic 216 calculates a known time domain cross-correlation between the signals $P_{asf1}$ and $P_{asf2}$ on the lines 212, 214, respectively, and provides an output signal on a line 218 indicative of the time delay $\tau$ it takes for an vortical flow field 188 (or vortex, stochastic, or vortical structure, field, disturbance or perturbation within the flow) to propagate from one sensing region 176 to the other sensing region 178. Such vortical flow disturbances, as is known, are coherent dynamic conditions that can occur in the flow which substantially decay (by a predetermined amount) over a predetermined distance (or coherence length) and convect (or flow) at or near the average velocity of the fluid flow. As described above, the vortical flow field 188 also has a stochastic or vortical pressure disturbance associated with it. In general, the vortical flow disturbances 188 are distributed throughout the flow, particularly in high shear regions, such as boundary layers (e.g., along the inner wall of the tube 14) and are shown herein as discrete vortical flow fields 188. Because the vortical flow fields (and the associated pressure disturbance) convect at or near the mean flow velocity, the propagation time delay $\tau$ is related to the velocity of the flow by the distance $\Delta X$ between the measurement regions 176,178, as discussed hereinafter.

The present invention uses temporal and spatial filtering to precondition the pressure signals to effectively filter out the acoustic pressure disturbances $P_{acoustic}$ and other long wavelength (compared to the sensor spacing) pressure disturbances in the tube 14 at the two sensing regions 176,178 and retain a substantial portion of the vortical pressure disturbances $P_{vortical}$ associated with the vortical flow field 188 and any other short wavelength (compared to the sensor spacing) low frequency pressure disturbances $P_{other}$. In accordance with the present invention, if the low frequency pressure disturbances $P_{other}$ are small, they will not substantially impair the measurement accuracy of $P_{vortical}$.

Another embodiment of the present invention includes a pressure sensor such as pipe strain sensors, accelerometers, velocity sensors or displacement sensors, discussed hereinafter, that are mounted onto a strap to enable the pressure sensor to be clamped onto the pipe. The sensors may be removable or permanently attached via known mechanical techniques such as mechanical fastener, spring loaded, clamped, clam shell arrangement, strapping or other equivalents. These certain types of pressure sensors, it may be desirable for the pipe 12 to exhibit a certain amount of pipe compliance.

Instead of single point pressure sensors 18-21, at the axial locations along the pipe 12, two or more pressure sensors may be used around the circumference of the pipe 12 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may be used. Averaging multiple annular pressure sensors reduces noises from disturbances and pipe vibrations and other sources of noise not related to the one-dimensional acoustic pressure waves in the pipe 12, thereby creating a spatial array of pressure sensors to help characterize the one-dimensional sound field within the pipe 12.

The pressure sensors 18-21 of FIG. 1 described herein may be any type of pressure sensor, capable of measuring the unsteady (or ac or dynamic ) pressures within a pipe 14, such as piezoelectric, optical, capacitive, resistive (e.g., Wheatstone bridge), accelerometers (or geophones), velocity measuring devices, displacement measuring devices, etc. If optical pressure sensors are used, the sensors 18-21 may be Bragg grating based pressure sensors, such as that described in U.S. patent application, Ser. No. 08/925,598, entitled "High Sensitivity Fiber Optic Pressure Sensor For Use In Harsh Environments", filed Sep. 8, 1997, now U.S. Pat. No. 6,016,702, and in U.S. patent application, Ser. No. 10/224,821, entitled "Non-Intrusive Fiber Optic Pressure Sensor for Measuring Unsteady Pressures within a Pipe", which are incorporated herein by reference. In an embodiment of the present invention that utilizes fiber optics as the pressure sensors 14 they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 15-18 and it may measure the unsteady (or dynamic or ac) pressure variations inside the tube 14 by measuring the pressure levels inside of the tube. These sensors may be ported within the pipe to make direct contact with the mixture 12. In an embodiment of the present invention, the sensors 14 comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves.

The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also within the scope of the present invention that any strain sensing technique may be used to measure the variations in strain in the pipe, such as highly sensitive piezoelectric, electronic or electric, strain gages and piezo-resistive strain gages attached to the pipe 12. Other strain gages include resistive foil type gages having a race track configuration similar to that disclosed U.S. patent application Ser. No. 09/344,094, filed Jun. 25, 1999, now U.S. Pat. No. 6,354,147, which is incorporated herein by reference. The invention also contemplates strain gages being disposed about a predetermined portion of the circumference of pipe 12. The axial placement of and separation distance $\Delta X_1$, $\Delta X_2$ between the strain sensors are determined as described herein above.

It is also within the scope of the present invention that any other strain sensing technique may be used to measure the variations in strain in the tube, such as highly sensitive piezoelectric, electronic or electric, strain gages attached to or embedded in the tube 14.

The present invention also contemplates the sensors 18-21 may be ultra-sonic sensors, especially, for measuring the vortical disturbances to determine the velocity of the flow, similar to that described in U.S. patent application Ser. No. 10/756,977, filed on Jan. 13, 2004, which is incorporated herein by reference.

Note that this entrained air or gas volume fraction measurement GVFgas 8 may be used with any flow meter to correct for errors introduced into a measurement by entrained air. For instance, an electromagnetic flow meter will show an error when entrained air exists in the mixture. The present invention may be used to correct for this error.

Referring to 15, the present invention contemplates an apparatus 300 for providing a volumetric flow measurement 11 that is compensated for entrained gas/air in the liquid or mixture 12. The apparatus 300 includes a device 302 for measuring the gas volume fraction of the mixture, which is substantially similar to that described herein before, and an electromagnetic flow meter 304 (also know as a Magmeter) for measuring the uncompensated volumetric flow rate of the mixture 12 within the pipe 14. As shown, the GVF device 302 provides a signal 8 indicative of the gas volume fraction of the mixture 12 to the electromagnetic flow meter 304. The magmeter 304 then compensates (or corrects) volumetric flow measurement 308 for entrained gas/air in response to the gas volume fraction signal 8. For example, this can be accomplished in accordance with the following equation:

Compensated Vol. Flow Rate=Vol. Flow Rate (1−Gas Volume Fraction)

The electromagnetic flow meter 308 may comprise an electromagnetic flow meter as described hereinbefore, such as that 8700 Series Magmeter manufactured by Rosemount. However, one will appreciate that the entrained air meter portion may used to compensate or correct any volumetric flow meter that is able to provide a volumetric flow meter measurement.

While the gas volume fraction signal 8 was provided to the magmeter 304 to compensate the volumetric flow rate, the invention contemplates that the correction for entrained gas/air may be performed in the GVF device 302.

Similarly, this GVF device 302 for measuring entrained air or gas volume fraction measurement GVFair 8 may be used with any consistency meter to correct for errors introduced into a measurement by entrained gas/air. For instance, a consistency meter will show an error when entrained air exists in the mixture. The present invention may be used to correct for this error.

Referring to 14, the present invention contemplates an apparatus 400 for providing a consistency measurement 11 that is compensated for entrained gas/air in the mixture or slurry 12 (e.g. paper/pulp slurry). The apparatus 300 includes a device 302 for measuring the gas volume fraction of the slurry 12, which is substantially similar to that described herein before, and a consistency meter 402 for measuring the uncompensated consistency measurement of the mixture 12 within the pipe 14. As shown, the GVF device 302 provides a signal 8 indicative of the gas volume fraction of the slurry 12 to the consistency meter 402. The consistency 402 then compensates (or corrects) consistency measurement 404 for entrained gas/air in response to the gas volume fraction signal 8. For example, this can be accomplished in accordance with the following equation:

Cmixture=Uncompensated Consistency Measurement−(1.4)(GVFair)

The consistency meter 402 may comprise a microwave consistency meter as described hereinbefore, such as that 8700 Series Magmeter manufactured by Rosemount. However, one will appreciate that the consistency meter portion may used to compensate or correct any consistency meter that is able to provide a consistency measurement.

Figure 16:
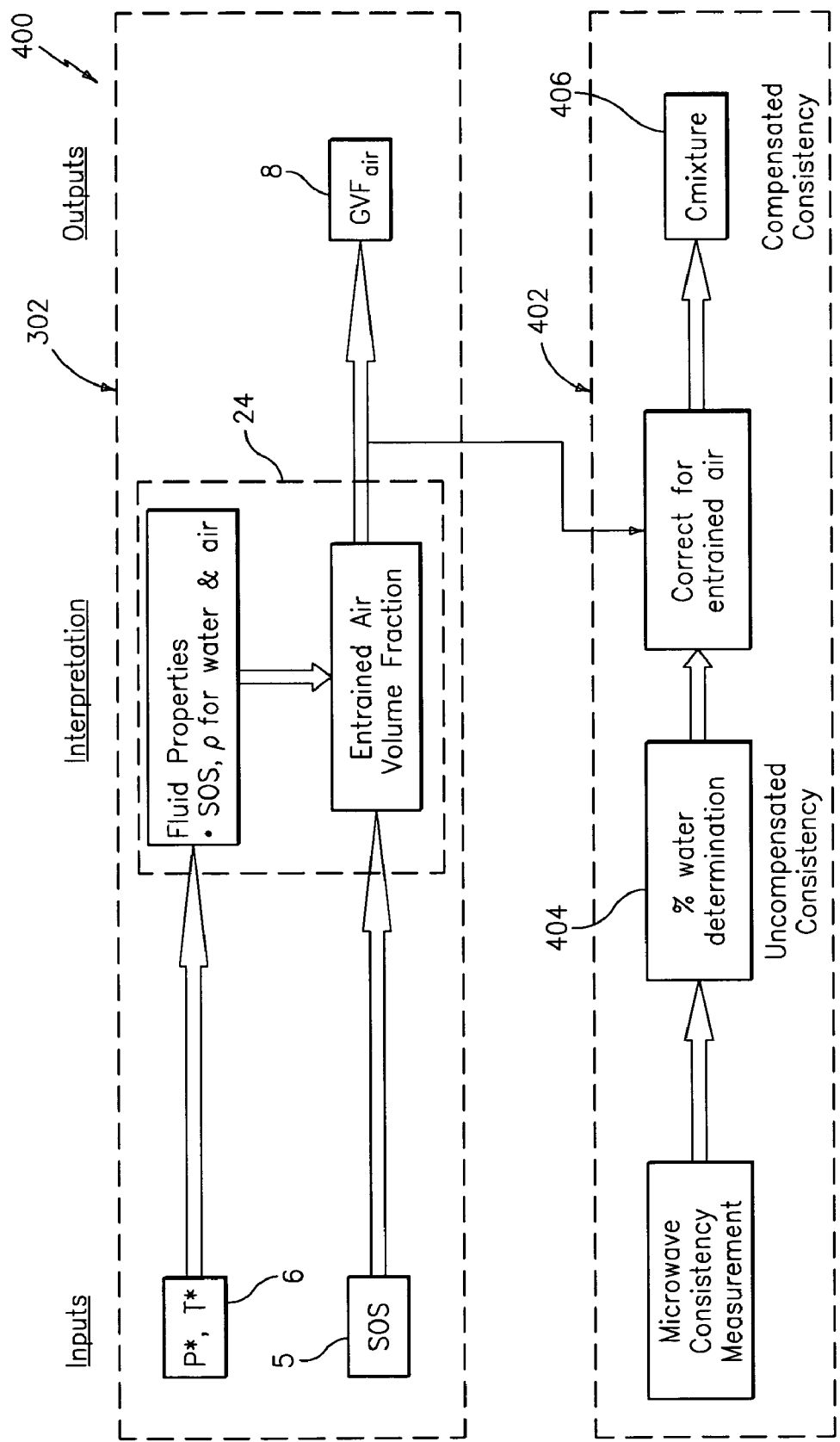
FIG. 16 is a functional flow diagram of an apparatus embodying the present invention that compensates the consistency measurement of a consistency meter, in accordance with the present invention.
Figure 17:
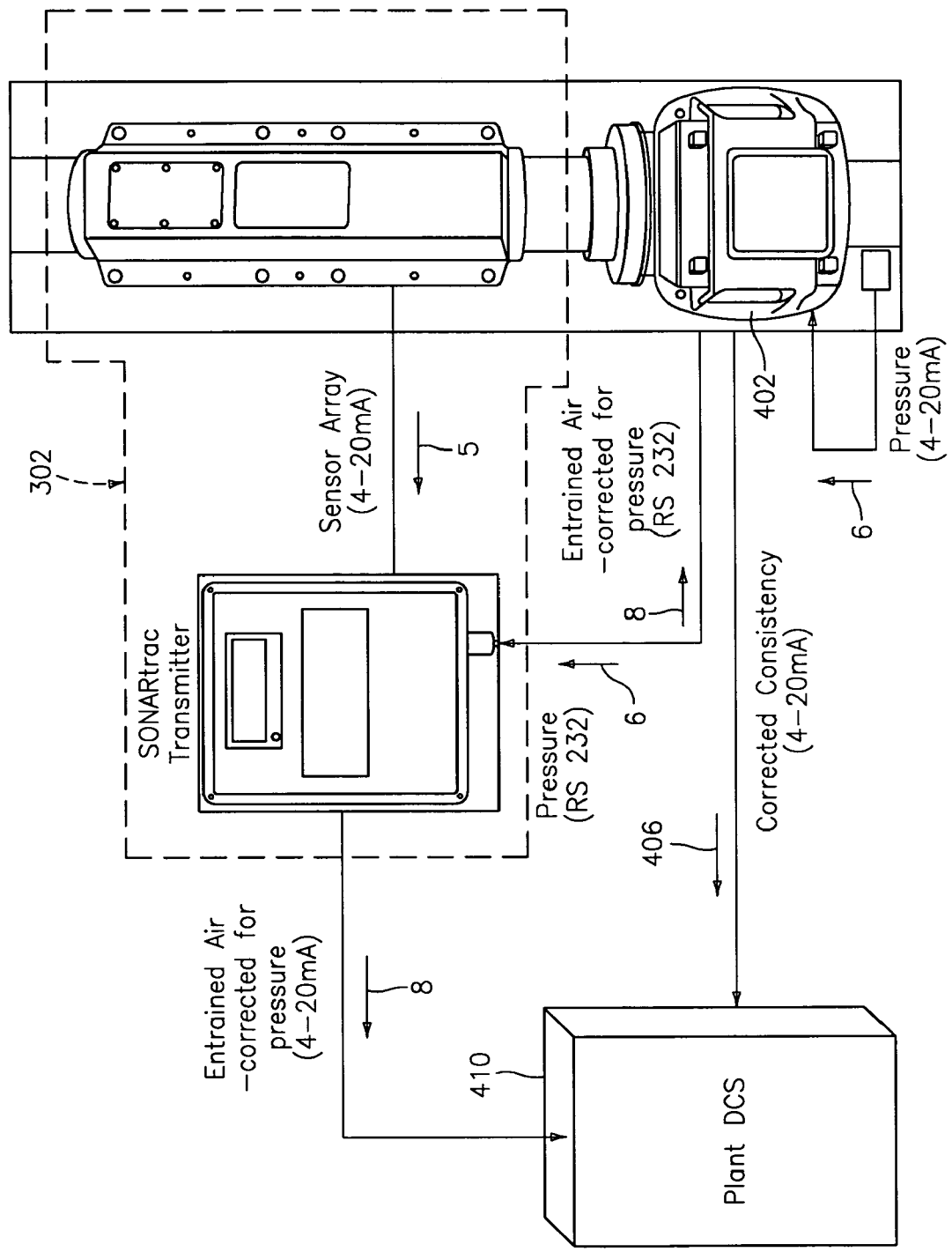
FIGS. 17-19 are configurations for an apparatus in accordance with the present invention.

While the gas volume fraction signal 8 was provided to the consistency meter 402 to compensate the consistency measurement as shown in FIG. 16, the invention contemplates that the correction for entrained gas/air may be performed in the GVF device 302. Referring to FIG. 17, the present invention contemplates the consistency meter 402 in accordance with the present invention receives and processes the measured pressure input 6 and the gas volume fraction input 8 (compensated for pressure) to provide a corrected consistency output 406 to the plant DCS 410.

Figure 18:
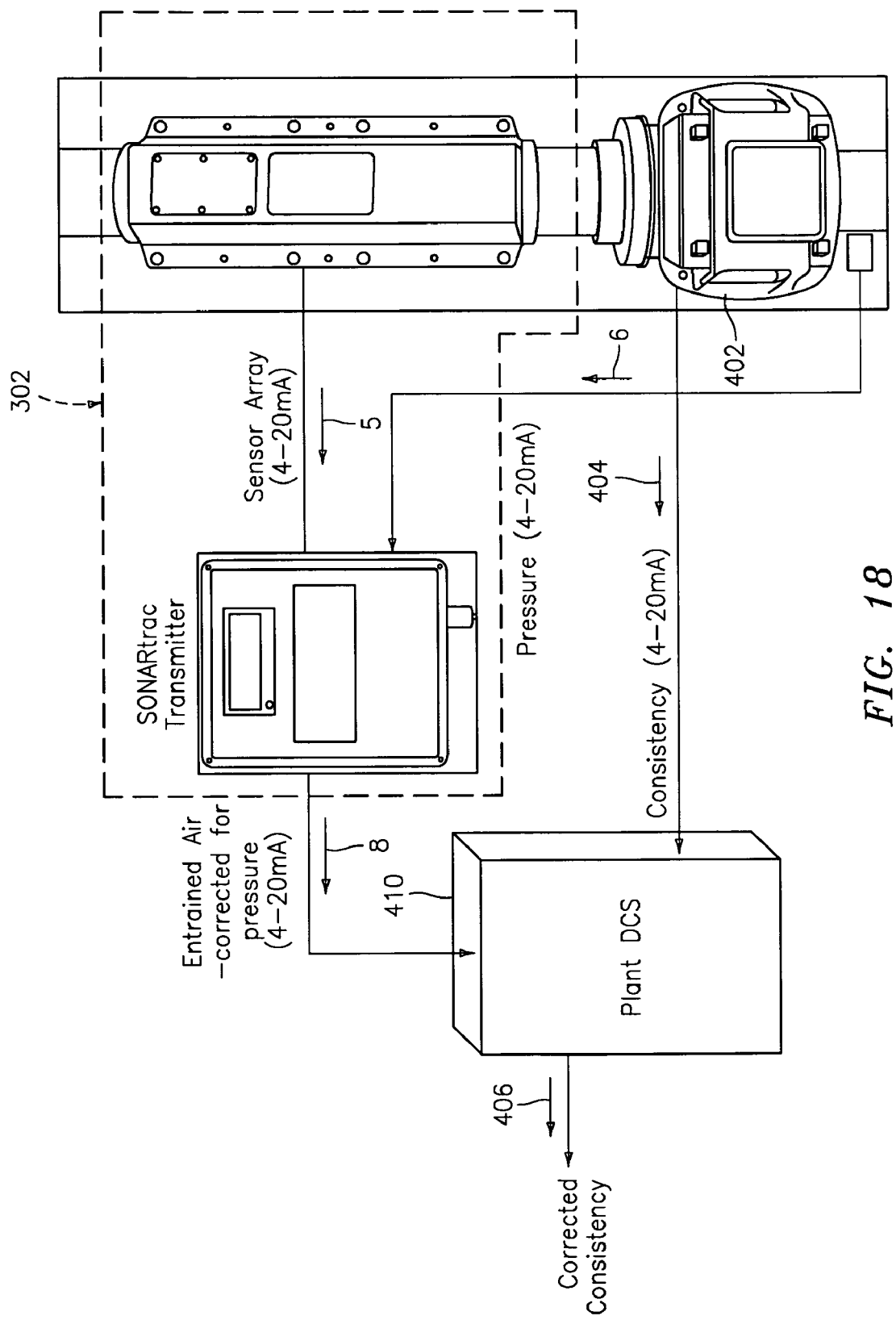
Figure 19:
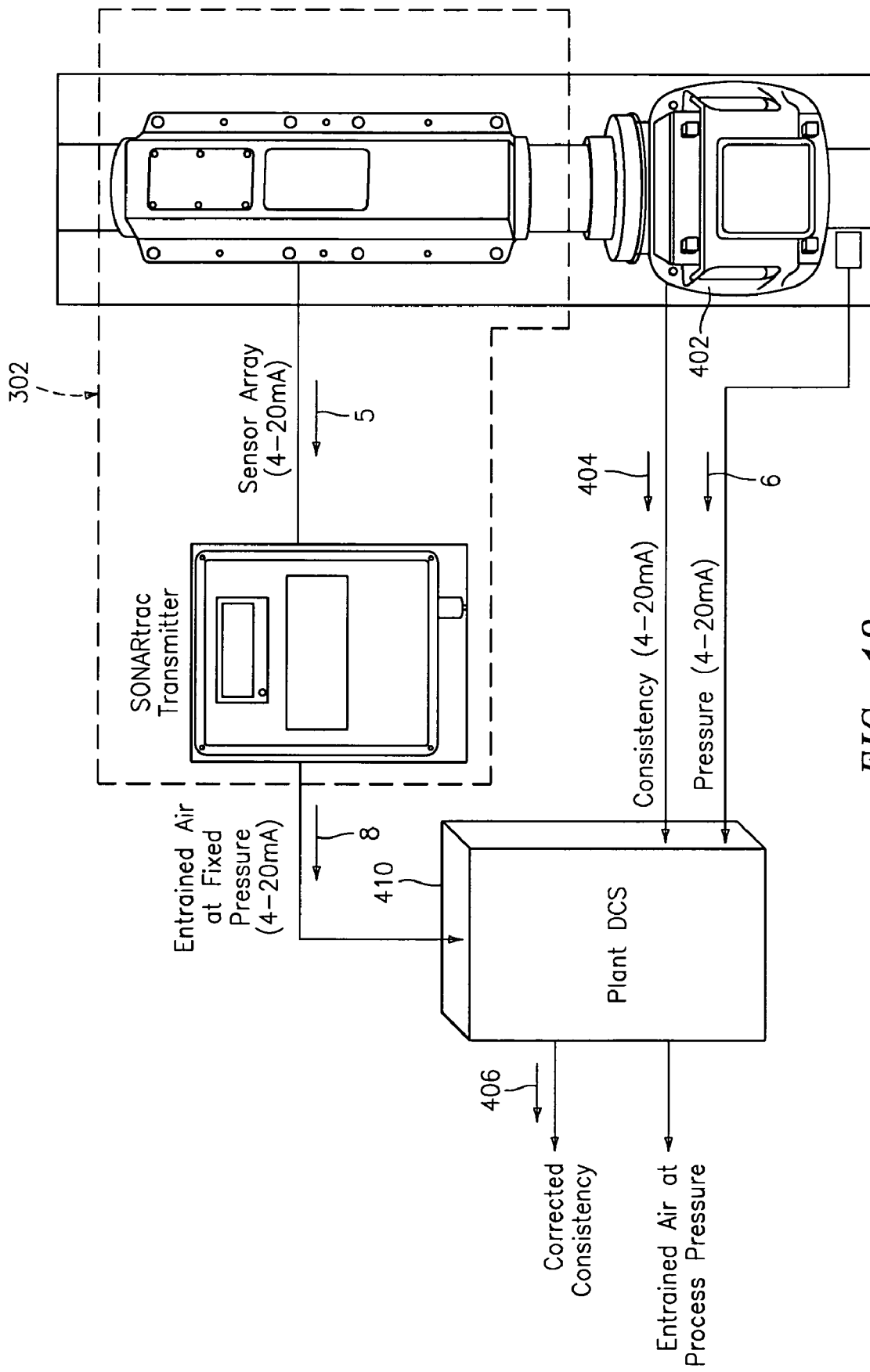

In FIG. 18, the plant DCS 410 in accordance with the present invention receives and process the uncorrected consistency measurement 404 from the consistency meter 402 and a GVF input 8 (compensated for pressure) and provides a corrected consistency output 406. In FIG. 19, the plant DCS 410 in accordance with the present invention receives and processes an uncorrected consistency measurement, a pressure measurement, and GVF measurement and provides a corrected consistency measurement 406 and a GVF measurement (compensated for process pressure).

Figure 20:
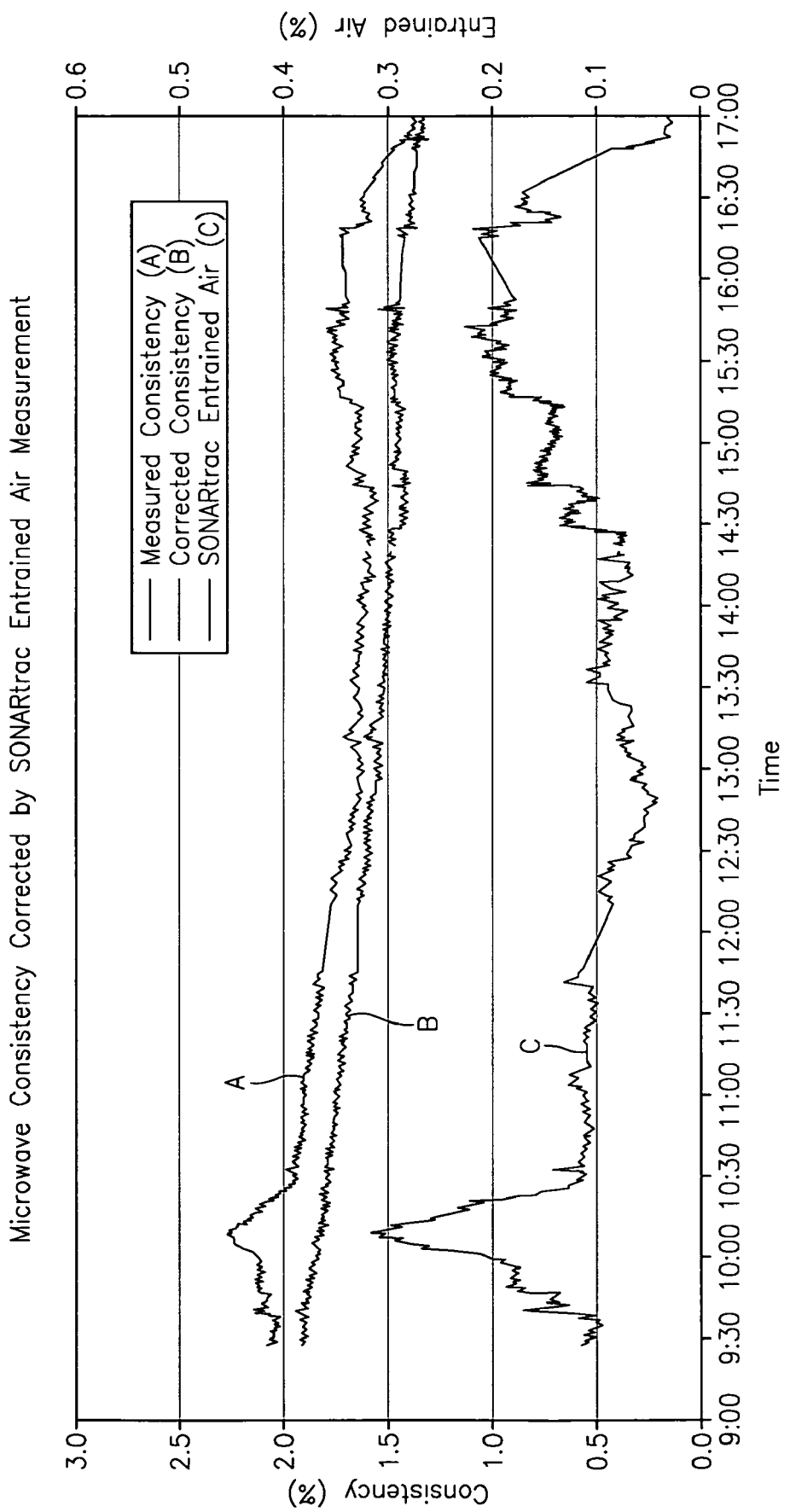
FIGS. 20-22 are plots of the output of an apparatus embodying the present invention for compensating a microwave consistency meter, in accordance with the present invention.
Figure 21:
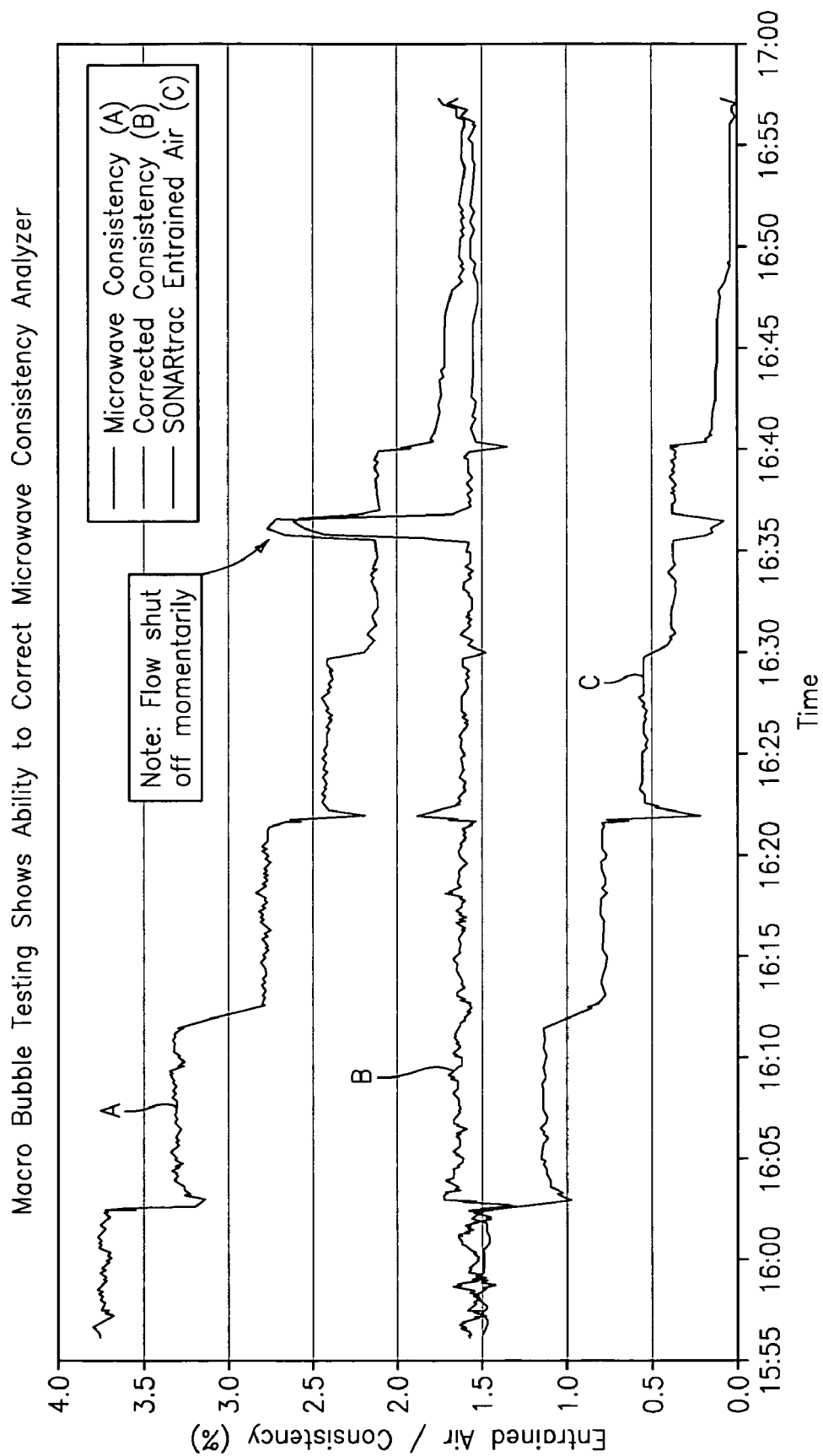
Figure 22:
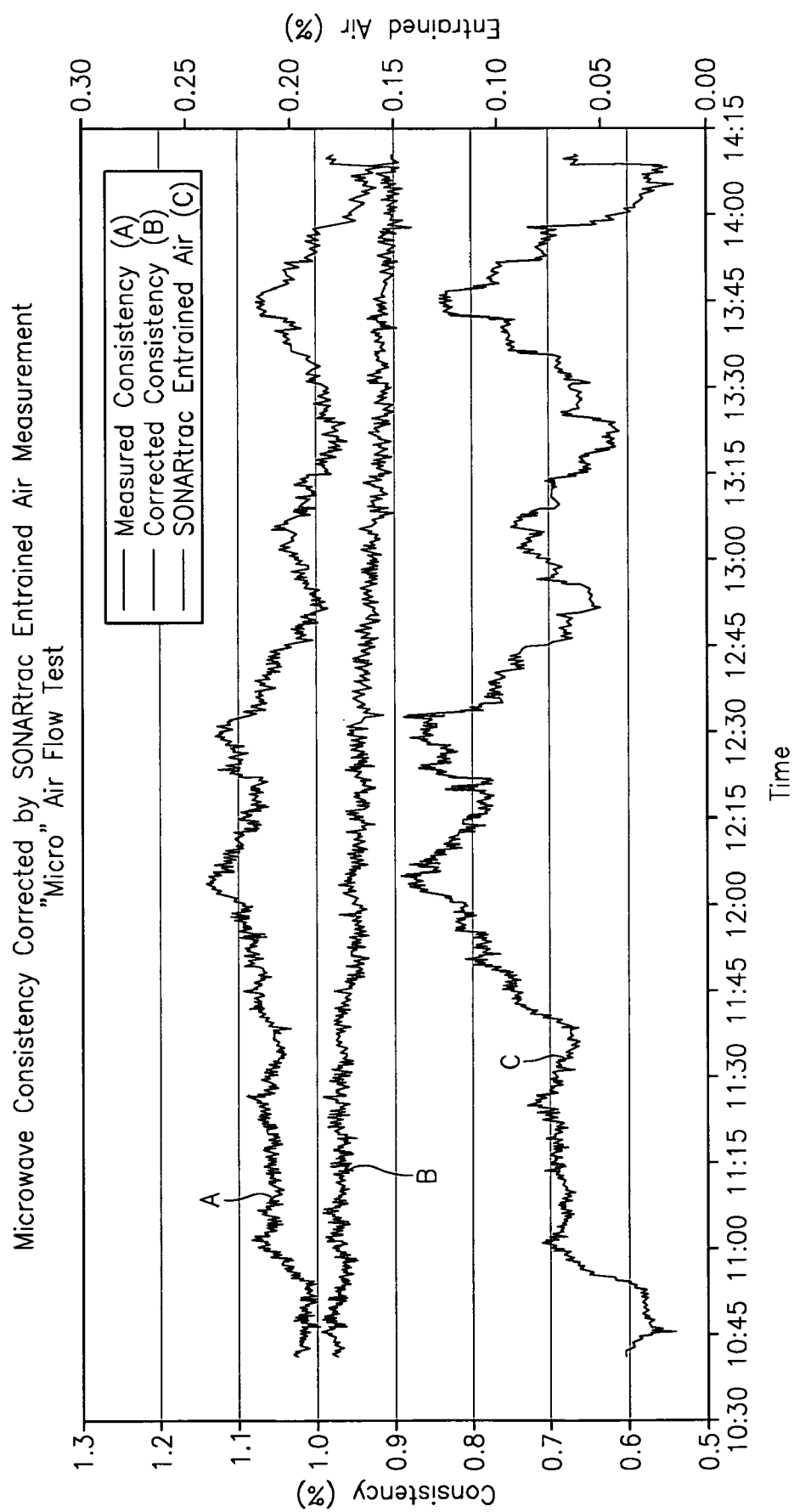

FIGS. 20-22 show data from an apparatus 400 in accordance with the present invention that measured and corrected for entrained air within a slurry propagating through a pipe. FIG. 20 shows the measured consistency from a consistency meter 402, the measured GVFair for a GVF meter 302 and the corrected consistency 406 over an eight hour time period. FIG. 21 shows the measured consistency from a consistency meter 402, the measured GVFair for a GVF meter 302 and the corrected consistency 406 for a slurry having macro-bubbles flowing therein. FIG. 22 shows the measured consistency from a consistency meter 402, the measured GVFair for a GVF meter 302 and the corrected consistency 406 for a slurry having micro-bubbles flowing therein. Consequently, as shown, the present invention eliminates the big bubble/small bubble analysis/compensation that other flow meters attempt to do to compensation for entrained gas/air in the process flow 12.

Microwave consistency analyzers (MCA) are commonly used in the paper making industry as the sensing element in a feedback loop designed maintain a preset consistency level within flow lines. The output of the MCA is used to control the mixing ratio between, typically, thick stock lines and dilution lines.

As developed previously, MCA rely on a "Speed of Light" measurement to determine the consistency of a pulp and water slurry. In the absence of entrained air, MCA meters are considered the most accurate consistency measuring devices available. However, using an MCA to control the consistency of approach lines in the presence of entrained air can be problematic. MCAs over-estimate consistency in the presence of entrained air. MCAs can over estimate the consistency of a pulp slurries by approximately 1.4 times the GVF in percent.

For processes that use MCAs to control consistency, the overestimate of consistency in the presence of entrained air can have direct impact on paper sheet strength and therefore paper breaks in the paper making process. Slurry consistency and entrained air each have an impact on paper strength and quality. In general, reducing consistency or increasing entrained air levels degrade the strength of the paper. Thus, for system controlling based on the output of a MCA, an unobserved increase in the entrained air will have a compounded effect on the paper quality. If unrecognized, the control system will see the increase in entrained air as an increase in measured consistency. The control loop will then increase the dilution water in an attempt maintain (i.e. lower) the measured consistency. Unfortunately, this action has the result of reducing the actual consistency to below intended levels during the periods of higher than average entrained air. The more the entrained air, the greater the problem becomes. This unintended coupling between entrained air and actual fiber content can lead to problems.

The problems posed by the coupling of entrained air and actual consistency in systems control with MCA can be further aggravated if the source of the entrained air is in the dilution water.

FIG. 23 illustrates a control loop 400 for controlling the consistency of a pulp and paper slurry, for example, having a mixing valve 404 for mixing a liquid into the process flow and a mixing valve 404 for mixing pulp into the process flow 12. A microwave consistency analyzer (or meter) 410 and a gas volume fraction meter 412, similar to that shown in FIG. 4, provide respective uncompensated consistency signal and gas volume fraction signal to a controller 406. The controller determines the compensated consistency measurement in light of the entrained gas in the process flow 12. In response to the compensated consistency measurement, the controller 406 provides respective control signals 408 to the mixing valves 402, 404 to ensure the consistency of the process flow 12 is maintained within a predetermined range. While the controller includes the processing of the data from the MCA and the GVF meter to determine compensated consistency, the invention contemplates that the GVF meter or MCA may process the data to determine the compensated consistency measurement, similar to that described hereinbefore.

Similarly, as shown in FIG. 24, a control loop 500 that includes a magmeter 510 and GVF meter 512, similar to that shown in FIG. 4, to provide a measurement of the flow rate of the process flow 12 and the gas volume fraction of the process flow, respectively. A controller 506 receives the data from the magmeter and the GVF meter and determines the compensated flow rate in light of the entrained gas in the process flow 12. In response to the flow rate measurement, the controller 506 provides a control signal 508 to a pump 502 to ensure the flow rate of the process flow 12 is maintained within a predetermined range. While the controller 506 includes processing the data from the magmeter 510 and the GVF meter 512 to determine the compensated flow rate, the invention contemplates that the GVF meter or flow meter may process the data to determine the compensated volumetric flow rate measurement, similar to that described hereinbefore.

While the control loops of FIGS. 23 and 24 show a microwave consistency meter and a magmeter, respectively, using a meter to measure the gas volume fraction to compensate for entrained gas within the flow, the present invention contemplates that the gas volume fraction meter can be used with any meter that measures a parameter of the flow that is effect by entrained gas in a flow loop.

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for measuring a parameter of a process flow having entrained gas flowing within a pipe, the apparatus comprising:
   a first meter including a sensor that provides a measurement signal indicative of a parameter of the flow propagating through the pipe;
   a second meter including a sensor that provides a phase fraction signal indicative of a gas phase fraction of the process flow; and
   a processor that determines a compensated measurement signal indicative of the measurement signal compensated for entrained gas in the process flow, in response to the measurement signal and the phase fraction signal.

2. The apparatus of claim 1, wherein the second meter includes at least two strain sensors disposed at different axial locations along the pipe, each of the strain sensors providing a respective strain signal indicative of acoustic pressure disturbances within the pipe at a corresponding axial position, wherein the second meter, responsive to said pressure signals, provides the phase fraction signal.

3. The apparatus of claim 2, wherein the second meter determines the slope of an acoustic ridge in the k-ω plane to determine the phase fraction signal.

4. The apparatus of claim 1, wherein the first meter includes at least two strain sensors at different axial locations along the pipe, each of the strain sensors providing a respective strain signal indicative of unsteady pressure disturbances within the pipe at a corresponding axial position, wherein the first meter, responsive to said strain signals, provides a signal indicative of a parameter of the process flow flowing within the pipe.

5. The apparatus of claim 4, wherein the parameter of the process flow is one of velocity of the process flow and/or the volumetric flow of the process flow.

6. The apparatus of claim 4, wherein the first meter determines the slope of a convective ridge in the k-ω plane to determine the velocity of the process flow flowing in the pipe.

7. The apparatus of claim 1, wherein the first meter is a volumetric flow meter and the measurement signal is indicative of the volumetric flow rate of the process flow.

8. The apparatus of claim 7, wherein the volumetric flow meter is an electromagnetic flow meter.

9. The apparatus of claim 1, wherein the first meter is a consistency flow meter and the measurement signal is indicative of the consistency of the process flow.

10. The apparatus of claim 9, wherein the consistency meter is a microwave consistency meter.

11. The apparatus of claim 1, wherein the compensated measurement signal is indicative of the volumetric flow rate of the non-aerated portion of the process flow.

12. The apparatus of claim 11, wherein the compensated measurement signal is determine by $Q_{comp}=Q_{meas}(1-\phi)$, where $Q_{comp}$ is the compensated measurement signal, $Q_{meas}$ is the measurement signal, and $\phi$ is the gas phase fraction of the process flow.

13. The apparatus of claim 1, wherein the measurement signal is indicative of the consistency of the process flow flowing in the pipe.

14. The apparatus of claim 1, wherein the compensated measurement signal is indicative of the consistency of the non-aerated portion of the process flow.

15. The apparatus of claim 14, wherein the compensated measurement signal is determine by $Q_{comp}=Q_{meas}(1-R\phi)$, where $Q_{comp}$ is the compensated measurement signal, $Q_{meas}$ is the measurement signal, R is a compensation factor, and $\phi$ is the gas volume fraction of the process flow.

16. The apparatus of claim 15, wherein the compensation factor is approximately 1.4.

17. The apparatus of claim 1, wherein the process flow is one of a liquid having entrained gas, a mixture having entrained gas, a liquid-liquid mixture having entrained gas, a liquid-solid mixture having entrained gas, and a slurry having entrained gas.

18. The apparatus of claim 1, wherein the first meter and second meter have at least one common sensor.

19. The apparatus of claim 1, wherein the second meter measures the speed of an one dimensional acoustic wave propagating through the process flow.

20. The apparatus of claim 1, wherein the second meter includes 3, 4, 5, 6, 7, 8, 9, 10, 11, 12, 13, 14, 15, or 16 sensors disposed at different axial locations along the pipe, each of the strain sensors providing a respective strain signal indicative of acoustic pressure disturbances within the pipe at a corresponding axial position, wherein the second meter, responsive to said pressure signals, provides the phase fraction signal.

21. The apparatus of claim 20, wherein the apparatus further includes at least one of a pressure sensor and temperature sensor to respective determine the pressure and temperature of the process flow.

22. A method for measuring a parameter of a process flow having entrained gas flowing within a pipe, the method comprising:

receiving a measurement signal indicative of a parameter of the process flow propagating through the pipe;

receiving a phase fraction measurement signal indicative of the gas phase fraction of the process flow; and determining a compensated measurement signal indicative of the measurement signal compensated for entrained gas in the process flow, in response to the measurement signal and the phase fraction signal.

23. An apparatus for measuring a parameter of a process flow having entrained gas flowing within a pipe, the apparatus comprising:

a first means for providing a measurement signal indicative of a parameter of the flow propagating through the pipe;

a second means for providing a phase fraction signal indicative of the gas phase fraction of the process flow; and a third means for determining a compensated measurement signal indicative of the measurement signal compensated for entrained gas in the process flow, in response to the measurement signal and the phase fraction signal.

* * * * *